(12) United States Patent
Coates et al.

(10) Patent No.: US 10,787,460 B2
(45) Date of Patent: *Sep. 29, 2020

(54) (E)-1-(4-(DIMETHYLAMINO)BUT-2-ENOYL) PYRROLIDIN-3-YL 4-((3-ISOPROPYL-5-METHYLPYRAZOLO [1,5-A]PYRIMIDIN-7-YL)AMINO) PIPERIDINE-1-CARBOXYLATE FOR INHIBITING CDK7

(71) Applicant: Eli Lilly and Company, Indianapolis, IN (US)

(72) Inventors: David Andrew Coates, New Palestine, IN (US); Carlos Montero, Madrid (ES); Bharvin Kumar Rameschandra Patel, Carmel, IN (US); David Michael Remick, Fishers, IN (US); Yipin Yadav, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/583,661

(22) Filed: Sep. 26, 2019

(65) Prior Publication Data

US 2020/0017513 A1    Jan. 16, 2020

Related U.S. Application Data

(63) Continuation of application No. 16/185,801, filed on Nov. 9, 2018, now Pat. No. 10,472,370.

(30) Foreign Application Priority Data

Nov. 16, 2017  (EP) .................................... 17382778
Jan. 23, 2018  (EP) .................................... 18382034
Jul. 20, 2018  (EP) .................................... 18382546

(51) Int. Cl.
*C07D 487/04*    (2006.01)
*A61P 35/00*     (2006.01)

(52) U.S. Cl.
CPC ............ *C07D 487/04* (2013.01); *A61P 35/00* (2018.01); *C07B 2200/13* (2013.01)

(58) Field of Classification Search
CPC .................................................. C07D 487/04
USPC ..................................................... 548/360.5
See application file for complete search history.

(56) References Cited

U.S. PATENT DOCUMENTS 10,472,370 B2 * 11/2019 Montero ................. A61P 35/00

FOREIGN PATENT DOCUMENTS

| WO | 2015154022 | 10/2015 |
|---|---|---|
| WO | 2016142855 | 9/2016 |
| WO | 2016160617 | 10/2016 |
| WO | 2016193939 | 12/2016 |
| WO | 2017044858 | 3/2017 |

OTHER PUBLICATIONS

Jordan, V. C. Nature Reviews: Drug Discovery, 2, 2003, 205.*
Hackann, et al. JAMA, 296(14), 2006, 1731-1732.*
International Search Report and Written Opinion for International Application No. PCT/US2018/060025 dated Feb. 4, 2019.
Caira M.R., "Crystalline Polymorphism of Organic Compounds. In: Weber E. et al. (eds)," Design of Organic Solids. Topics in Current Chemistry, vol. 198, pp. 163-208 (1998).

* cited by examiner

Primary Examiner — Douglas M Willis
(74) Attorney, Agent, or Firm — Bradley W. Crawford

(57) ABSTRACT

The present invention provides novel CDK7 inhibitors and pharmaceutical compositions thereof:

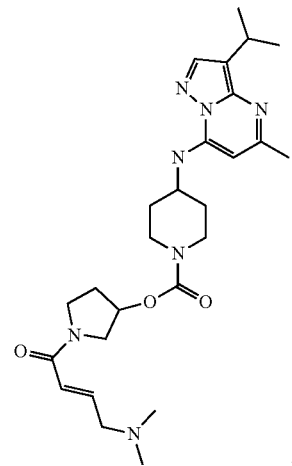

or a pharmaceutically acceptable salt thereof.

17 Claims, No Drawings
Specification includes a Sequence Listing.

(E)-1-(4-(DIMETHYLAMINO)BUT-2-ENOYL) PYRROLIDIN-3-YL 4-((3-ISOPROPYL-5-METHYLPYRAZOLO[1,5-A]PYRIMIDIN-7-YL)AMINO)PIPERIDINE-1-CARBOXYLATE FOR INHIBITING CDK7

The present invention relates to compounds useful for inhibiting cyclin-dependent kinase 7 (CDK7), pharmaceutical compositions, and methods for treating diseases related to CDK7 activity.

Cyclin-dependent kinases (CDKs) are a major class of kinases and are important in cancer cell proliferation and deregulated oncogenic transcription. CDK7 binds to cyclin H and MAT1 to form a trimeric cyclin-activating kinase (CAK) that performs its function by phosphorylating other CDKs involved in cell-cycle control. These complexes control specific transitions between two subsequent phases in the cell cycle. CDK7 is implicated in both temporal control of the cell cycle and transcriptional activity. CDK7 is implicated in the transcriptional initiation process by phosphorylation of Rbp1 subunit of RNA Polymerase II (RNA-PII). Uncontrolled cell proliferation and deregulated transcription is a cancer hallmark. Targeting CDK7 selectively may offer an advantage by simultaneously inhibiting active transcription and cell-cycle progression. Therefore, CDK7 is a promising target for the treatment of cancer, in particular aggressive and hard-to-treat cancers.

Small molecule inhibitors against CDK7 have been reported in the literature (see, e.g., WO 2015/154022, WO 2016/142855, WO 2016/160617, WO 2016/193939, and WO 2017/044858). There remains a need to provide CDK7 inhibitors which can be used in the treatment of cell proliferative disorders, such as cancer. Additionally, there is a need to provide CDK7 inhibitors which are selective for CDK7 compared to other CDKs.

The present invention provides novel compounds that are selective CDK7 inhibitors. Such new compounds could address the need for potent, effective treatment of cancer, especially cancer with deregulated transcription. The present invention could also address the need for potent, effective treatment of urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, and/or gliomas.

The present invention provides a compound of formula:

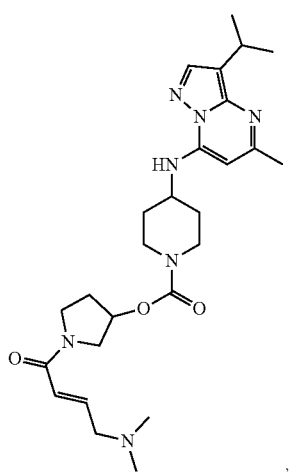 [SMILES: Cc1cc(NC2CCN(C(=O)OC3CCN(C(=O)/C=C/CN(C)C)C3)CC2)n2ncc(C(C)C)c2n1]

or a pharmaceutically acceptable salt thereof. Especially preferred is a besylate salt. Also preferred is the hemi-edisylate hydrate salt.

The present invention also provides a method for the treatment of cancer, in particular for the treatment of cancer with deregulated transcription. Preferably, the cancer is urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas. More preferably, the cancer is colorectal cancer, breast cancer, lung cancer, ovarian cancer, or gastric cancer. Most preferably, the cancer is breast cancer.

The present invention also provides a method of treating urothelial cancer, uterine cancer, colorectal cancer, breast cancer, lung cancer, ovarian cancer, gastric cancer, hepatobiliary cancer, urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas in a patient, comprising testing for the presence of at least one loss of function mutation in the ARID1A, KMT2C, KMT2D and/or RB1 genes in a biological sample from the patient and administering a therapeutically effective amount of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to the patient if the sample tests positive for at least one loss of function mutation in any of the ARID1A, KMT2C, KMT2D and/or RB1 genes. Preferably, the salt is a besylate salt or a hemi-edisylate hydrate salt. More preferably, the cancer is colorectal cancer, breast cancer, lung cancer, ovarian cancer, or gastric cancer. Most preferably, the cancer is breast cancer. Preferably, the biological sample is a tumor sample and the sample is assayed by genomic/DNA sequencing. Preferably, the sample is obtained from the patient prior to a first administration of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to the patient. Preferably, the salt is a besylate salt or a hemi-edisylate hydrate salt. Preferably, the gene is the ARID1A gene. Preferably, the gene is the KMT2C gene. Preferably, the gene is the KMT2D gene. Preferably, the gene is the RB1 gene.

The present invention also provides a method of treating urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas in a patient, comprising administering a therapeutically effective amount of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to the patient provided that a biological sample from the patient contains at least one loss of function mutation in the ARID1A, KMT2C, KMT2D and/or RB1 genes. Preferably, the salt is a besylate salt of a hemi-edisylate hydrate salt. More preferably, the cancer is colorectal cancer, breast cancer, lung cancer, ovarian cancer, or gastric cancer. Most preferably, the cancer is breast cancer. Preferably, the biological sample is a tumor sample and the sample is assayed by genomic/DNA sequencing. Preferably, the sample is obtained from the patient prior to a first administration of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to the patient. Preferably, the salt is a besylate salt or a hemi-edisylate hydrate salt. Preferably, the gene is the ARID1A gene. Preferably, the gene is the KMT2C gene. Preferably, the gene is the KMT2D gene. Preferably, the gene is the RB1 gene.

The present invention also provides a method of treating urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas in a patient, comprising administering a therapeutically effective amount of [(3S)-1-[(E)-4-(dimethylamino) but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to a patient provided that the patient is selected for treatment if a biological sample from the patient tested positive for at least one loss of function mutation in the ARID1A, KMT2C, KMT2D and/or RB1 genes. Preferably, the salt is a besylate salt or a hemi-edisylate hydrate salt. More preferably, the cancer is selected from the group consisting of colorectal cancer, breast cancer, lung cancer, ovarian cancer, or gastric cancer. Most preferably, the cancer is breast cancer. Preferably, the biological sample is a tumor sample and the sample is assayed by genomic/DNA sequencing. Preferably, the sample is obtained from the patient prior to a first administration of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate or a pharmaceutically acceptable salt thereof to the patient. Preferably, the salt is a besylate salt or hemi-edisylate hydrate salt. Preferably, the gene is the ARID1A gene. Preferably, the gene is the KMT2C gene. Preferably, the gene is the KMT2D gene. Preferably, the gene is the RB1 gene.

The present invention also provides a pharmaceutical composition comprising a compound of the invention, or a pharmaceutically acceptable salt thereof, in combination with one or more pharmaceutically acceptable carriers, diluents, or excipients. In a further embodiment, the composition further comprises one or more other therapeutic agents. In a further embodiment, the present invention provides a pharmaceutical composition for the treatment of cancer comprising a compound of the invention, or a pharmaceutically acceptable salt thereof, in combination with one or more pharmaceutically acceptable carriers, diluents, or excipients. In yet a further embodiment, the present invention provides a pharmaceutical composition for the treatment of cancer with deregulated transcription comprising a compound of the invention, or a pharmaceutically acceptable salt thereof, in combination with one or more pharmaceutically acceptable carriers, diluents, or excipients. In said embodiments, the cancer is urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas.

In a preferred embodiment, the cancer is colorectal cancer, breast cancer, lung cancer, ovarian cancer, or gastric cancer. In a more preferred embodiment, the cancer is breast cancer.

Further, the present invention provides a compound of the invention or a pharmaceutically acceptable salt thereof, for use in the treatment of cancer also comprising performing an in vitro assay using a biological sample from the patient, determining the presence of at least one inactivating mutation in the ARID1A, KMT2C, KMT2D and RB1 genes, and administering a therapeutically effective amount of the compound or salt thereof to the patient if at least one inactivating mutation in any of the genes is present. In said embodiment, the cancer is for use in the treatment of urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas. Preferably, the biological sample is a tumor sample and the sample is assayed by genomic/DNA sequencing. Preferably, the compound of salt thereof is administered to the patient at a dose of about 1 mg to 2 g. Preferably, the sample is obtained from the patient prior to the first administration of the compound or the salt thereof to the patient. Preferably, a patient is selected from having an inactivating mutation in the ARID1A gene. Preferably, the patient is selected for having an inactivating mutation in the KMT2C gene. Preferably, a patient is selected for having an inactivating mutation in the KMT2D gene. Preferably, a patient is selected for having an inactivating mutation in the RB1 gene.

Further, the present invention provides a compound of the invention, or a pharmaceutically acceptable salt thereof, for use in therapy, in particular for the treatment of cancer with deregulated transcription. In a further embodiment, the present invention provides the use of a compound of the invention, or a pharmaceutically acceptable salt thereof, for the manufacture of a medicament for the treatment of cancer with deregulated transcription. In said embodiments, the cancer is urothelial cancer, uterine cancer, colorectal cancer, breast cancer, lung cancer, ovarian cancer, gastric cancer, hepatobiliary cancer, pancreatic cancer, cervical cancers, prostate cancer, haematological cancers, sarcomas, skin cancers, or gliomas. In a preferred embodiment, the cancer is selected colorectal cancer, breast cancer, lung cancer, ovarian cancer, or gastric cancer. In a more preferred embodiment, the cancer is breast cancer.

In yet a further embodiment, the present invention provides a compound of the invention, or a pharmaceutically acceptable salt thereof, for use in therapy, in particular for the treatment of cancer. In a further embodiment, the present invention provides the use of a compound of the invention, or a pharmaceutically acceptable salt thereof, for the manufacture of a medicament for the treatment of cancer. In said embodiments, the cancer is urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas. In a preferred embodiment, the cancer is colorectal cancer, breast cancer, lung cancer, ovarian cancer, or gastric cancer. In a more preferred embodiment, the cancer is breast cancer. Further, the present invention provides for the manufacture of a medicament for the treatment of a urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas, also comprising performing an in vitro assay using a biological sample from the patient, determining the presence of at least one inactivating mutation in the ARID1A, KMT2C, KMT2D and RB1 genes, and administering a therapeutically effective amount of the compound or salt thereof to the patient if at least one inactivating mutation in any of the genes is present. Preferably, the biological sample is a tumor sample and the sample is assayed by genomic/DNA sequencing. Preferrably the compound of salt thereof is administered to the patient at a dose of about 1 mg to 2 g. Preferably, the sample is obtained from the patient prior to the first administration of the compound or the salt thereof to the patient. Preferably, a patient is selected for having at least one inactivating mutation in the ARID1A gene. Preferably, a patient is selected for having at least one inactivating mutation in the KMT2C gene. Preferably, a patient is selected for having at least one inactivating mutation in the KMT2D gene. Preferably, a patient is selected for having at least one inactivating mutation in the RB1 gene.

The present invention provides a compound of the invention [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate in a crystalline salt form. The present invention also provides crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hemi-edisylate hydrate. The present invention also provides [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hemi-edisylate hydrate in a crystalline form characterized by a X-ray powder diffraction pattern having characteristic peaks using CuKa radiation, in 2θ±0.2°, occurring at 18.5° in combination with one or more peaks selected from the group consisting of 21.5°, 16.7°, and 15.2°. The present invention also provides crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate besylate. The present invention also provides [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate besylate in a crystalline form characterized by a X-ray powder diffraction pattern having characteristic peaks using CuKa radiation, in 2θ±0.2°, occurring at 21.5° in combination with one or more peaks selected from the group consisting of 12.4°, 17.3°, and 15.8°. The present invention also provides crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hydrochloride. The present invention also provides [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hydrochloride in a crystalline form characterized by a X-ray powder diffraction pattern having characteristic peaks using CuKa radiation, in 2θ±0.2°, occurring at 18.9° in combination with one or more peaks selected from the group consisting of 5.5°, 15.5°, and 9.7°.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

As used herein, the terms "cancer" and "cancerous" refer to or describe the physiological condition in patients that is typically characterized by unregulated cell proliferation. Included in this definition are benign and malignant cancers. By "early stage cancer" or "early stage tumor" is meant a cancer that is not advanced or metastatic or is classified as a Stage 0, I, or II cancer. Examples of cancer include, but are not limited to, urothelial cancer, uterine cancer, colorectal cancer, breast cancer, lung cancer, ovarian cancer, gastric cancer, hepatobiliary cancer, pancreatic cancer, cervical cancers, prostate cancer, haemotological cancers, sarcomas, skin cancers, or gliomas.

A compound of the present invention may react to form pharmaceutically acceptable salts. Pharmaceutically acceptable salts and common methodology for preparing them are well known in the art (see, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

The skilled artisan will appreciate that a compound of the invention, as shown in (I), or pharmaceutically acceptable salt thereof, is comprised of a core that contains one chiral center, as represented by * below:

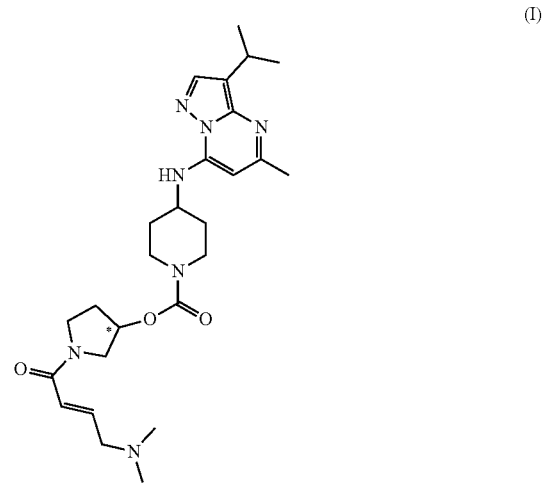

(I)

Although the present invention contemplates all individual enantiomers, as well as mixtures of the enantiomers of said compounds including racemates, the preferred compound of the invention is represented by (II) below:

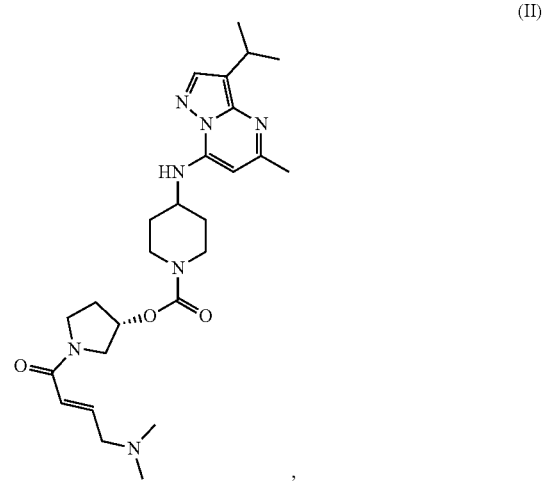

(II)

or pharmaceutically acceptable salts thereof.

The skilled artisan will also appreciate that the Cahn-Ingold-Prelog (R) or (S) designations for all chiral centers will vary depending upon the substitution patterns of the particular compound. The single enantiomers may be prepared beginning with chiral reagents or by stereoselective or stereospecific synthetic techniques. Alternatively, the single enantiomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes. Such pharmaceutical compositions and processes for preparing the same are well known in the art (see, e.g., *Remington: The Science and Practice of Pharmacy* (A. Gennaro, et al., eds., 21st ed., Mack Publishing Co., 2005)). More particularly preferred, is a pharmaceutical composition comprising a compound of the formula,

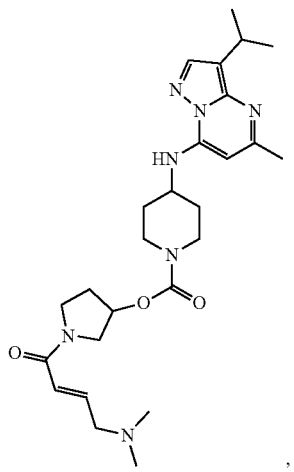

(I)

or a pharmaceutically acceptable salt thereof and one or more pharmaceutically acceptable carriers or diluents.

A preferred embodiment of the present invention is

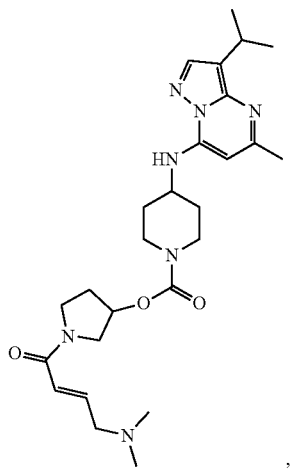

(I)

or a pharmaceutically acceptable salt thereof.

An especially preferred embodiment of the present invention relates to the compound, (3S)-1-[(2E)-4-(Dimethylamino)but-2-enoyl]pyrrolidin-3-yl 4-{[5-methyl-3-(propan-2-yl)pyrazolo[1,5-a]pyrimidin-7-yl]amino}piperidine-1-carboxylate:

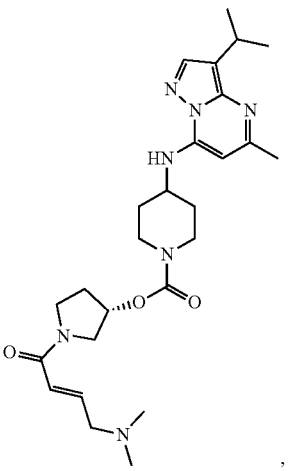

(II)

or a pharmaceutically acceptable salt thereof. Especially preferred in the hemi-edisylate hydrate salt or besylate salt.

Another especially preferred embodiment of the present invention relates to the compound, (3S)-1-[(2E)-4-(Dimethyl amino)but-2-enoyl]pyrrolidin-3-yl 4-{[5-methyl-3-(propan-2-yl)pyrazolo[1,5-A]pyrimidin-7-yl]amino}piperidine-1-carboxylate:

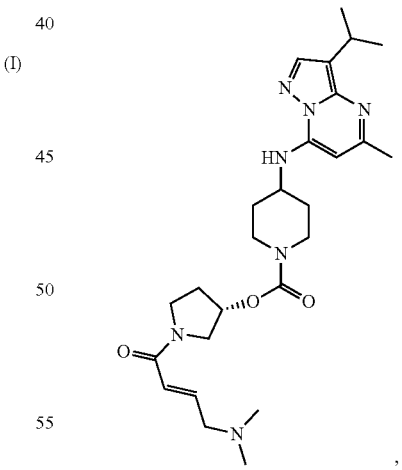

(II)

A further especially preferred embodiment of the present invention relates to the compound, (3R)-1-[(2E)-4-(Dimethylamino)but-2-enoyl]pyrrolidin-3-yl 4-{[5-methyl-3-(propan-2-yl)pyrazolo[1,5-A]pyrimidin-7-yl]amino}piperidine-1-carboxylate (as shown by (III) below):

(III)

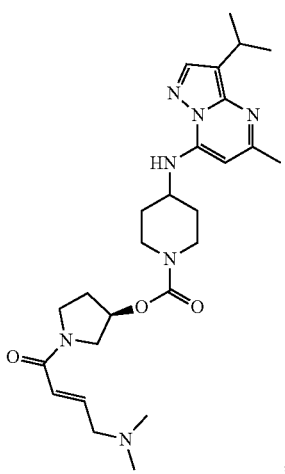

or a pharmaceutically acceptable salt thereof. Especially preferred in the hemi-edisylate hydrate salt or besylate salt.

Another especially preferred embodiment of the present invention relates to the compound, (3R)-1-[(2E)-4-(Dimethylamino)but-2-enoyl]pyrrolidin-3-yl 4-{[5-methyl-3-(propan-2-yl)pyrazolo[1,5-A]pyrimidin-7-yl]amino}piperidine-1-carboxylate:

(III)

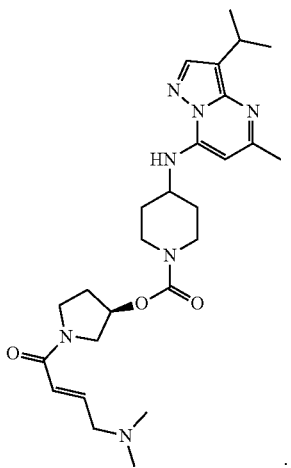

The compounds of the present invention are generally effective over a wide dosage range. For example, dosages per day fall within the range of about 1 mg to about 2 g. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in light of the relevant circumstances, including the condition to be treated, the chosen route of administration, the actual compound or compounds administered, the age, weight, and response of the individual patient, and the severity of the patient's symptoms.

Individual isomers and enantiomers may be separated or resolved by one of ordinary skill in the art at any convenient point in the synthesis of compounds of the invention, by methods such as selective crystallization techniques or chiral chromatography (see, for example, J. Jacques, et al., "Enantiomers, Racemates, and Resolutions", John Wiley and Sons, Inc., 1981, and E. L. Eliel and S. H. Wilen," Stereochemistry of Organic Compounds", Wiley-Interscience, 1994).

Additionally, certain intermediates described herein may contain one or more protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Certain abbreviations are defined as follows: "$^1$H NMR" refers to $^1$H-nuclear magnetic resonance; "eq" refers to equivalent; "THF" refers to tetrahydrofuran; "DCM" refers to dichloromethane; "MeCN" or "ACN" refers to acetonitrile; "DMSO" refers to dimethyl sulfoxide; "MTBE" refers to methyl tert-butyl ether; "TEA" refers to trimethylamine; "HATU" refers to I-[Bis(dimethylamino)methylene]-I 8-1, 2,3-triazolo[4, 5-b]pyridinium 3-oxid-hexafluorophosphate; "MeOH" refers to methanol; "TLC" refers to thin layer chromatography; "UV" refers to ultraviolet; "LC Column" refers to liquid chromatography column; "DMEA" refers to dimethylmethylamine; "EtOAc" refers to ethyl acetate; "DMF" refers to dimethylformamide; "SCX" refers to strong cation exchange; "ca." refers to about or approximately; "RBF" refers to round bottom flask; "ATP" refers to adenosine triphosphate; "DTT" refers to dithiothreitol; "HEPES" refers to (4-(2-hydroxyethyl)-1-piperazineethanesulfonic acid); "EDTA" refers to Ethylenediaminetetraacetic acid; "ATCC" refers to American Type Culture Collection; "RT" refers to room temperature; "PBS" refers to phosphate-buffered saline; "BSA" refers to bovine serum albumin; "FBS refers to fetal bovine serum; "RNAase" refers to ribonuclease; "cDNA" refers to complementary DNA; "GST" refers to glutathione S-transferase; "His" refers to histidine; "GSH" refers to glutathione; and "HBSS" refers to Hank's Balanced Salt Solution.

The compounds of the invention, or pharmaceutically acceptable salts thereof, may be prepared by a variety of procedures known in the art, as well as the Preparations and Examples below. The specific synthetic steps for each of the routes described may be combined in different ways, or in conjunction with steps from different schemes, to prepare compounds of the invention, or pharmaceutically acceptable salts thereof. The products of each step in the schemes below can be recovered by conventional methods well known in the art, including extraction, evaporation, precipitation, chromatography, filtration, trituration, and crystallization. The reagents and starting materials are readily available to one of ordinary skill in the art.

The following preparations and examples further illustrate the invention and represent typical synthesis of the compounds of the present invention.

PREPARATIONS AND EXAMPLES

Preparation 1

Synthesis of 3-isopropylpyrazolo[1,5-a]pyrimidine-5,7-diol

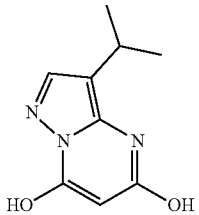

Add sodium ethoxide (979 g, 14.4 moles, 3.0 eq) and diethyl malonate (998 g, 6.23 moles, 3.0 eq) at 23° C. to a solution of 4-isopropyl-1H-pyrazol-3-amine (600 g, 4.79 moles) in ethanol (4.2 L) and heat the mixture to 80° C. (internal temperature) for 15 hours. Cool the mixture to 25° C., add 1 M aq. HCl (2.0 L) (final pH=2.0), filter, wash the solid with water (2.0 L), and dry to obtain 3-isopropylpyrazolo[1,5-a]pyrimidine-5,7-diol (600 g, 65%) as a white solid. ES/MS m/z 194 (M+H).

Preparation 2

Synthesis of 5,7-dichloro-3-isopropyl-pyrazolo[1,5-a]pyrimidine

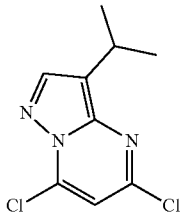

Add POCl$_3$ (2.00 L, 25.8 moles, 10 eq) and N,N-dimethylaniline (162 mL, 2.58 moles, 1.0 eq) to a suspension of 3-isopropylpyrazolo[1,5-a]pyrimidine-5,7-diol (500 g, 2.58 moles) in MeCN (1.25 L) at 50° C. and heat the mixture to 100° C. for 36 hours. Cool to 23° C., pour dropwise into 1:1 ice/phosphate buffer (1 M, pH=8, 10 L) and stir for 15 hours. Filter, wash the solid with water (5.0 L) and dry to obtain 5,7-dichloro-3-isopropyl-pyrazolo[1,5-a]pyrimidine (375 g, 63%) as a brown solid. ES/MS m/z ($^{35}$Cl/$^{37}$Cl) 230/232 (M+H). $^1$H NMR (d$_6$-DMSO) δ 1.32 (d, 6H), 3.19 (dq, 1H), 7.58 (s, 1H), 8.31 (s, 1H).

Alternative Synthesis of 5,7-dichloro-3-isopropyl-pyrazolo[1,5-a]pyrimidine

Add sodium ethoxide—21% in ethanol—(17.9 mL, 47.9 mmol) to a solution of 4-isopropyl-1H-pyrazol-5-amine (5 g, 39.9 mmol) and diethyl malonate (6.74 mL, 43.9 mmol) in ethanol (150 mL) and stir at RT. After 5 minutes, heat at 90° C. and stir. After 18 hours, cool to RT and concentrate under reduce pressure. Dissolve the residue with water and add 1 N hydrochloric acid to pH=3. Filter the white precipitate and dry under reduced pressure at 50° C. for 18 hours. Suspend the resulting solid, 3-isopropylpyrazolo[1,5-a]pyrimidine-5,7-diol (4.92 g, 25.5 mmol, 0.638) in phosphorous oxychloride (48 mL) and add N,N-dimethylaniline (2.3 mL). Reflux the mixture at 110° C. After 2 hours, cool to RT and concentrate under reduced pressure. Pour the residue onto an ice/water solution and extract with DCM (twice). Combine the organic layers and wash with brine, dry over magnesium sulfate. Filter, and concentrate under reduced pressure to give a residue. Purify the residue by flash chromatography (silica gel), eluting with ethyl hexane:acetate to provide 5,7-dichloro-3-isopropyl-pyrazolo[1,5-a]pyrimidine (4.45 g, 19.3 mmol) as a brown solid. MS (m/z): 230,232 (M+1). $^1$H NMR (400.21 MHz, DMSO): 8.31 (s, 1H), 7.58 (s, 1H), 3.19 (m, 1H), 1.32 (d, J=7.0 Hz, 6H).

Preparation 3

Synthesis of Tert-Butyl 4-[(5-chloro-3-isopropyl-pyrazolo[1,5-a]pyrimidin-7-yl)amino]piperidine-1-carboxylate

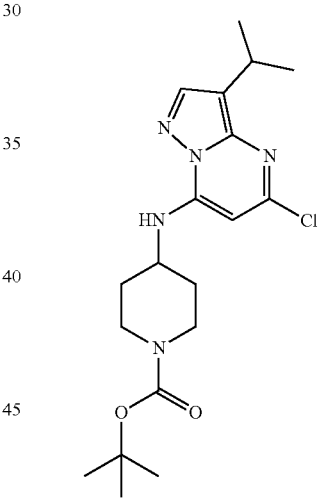

Add N,N-diisopropylethylamine (189 mL, 140 g, 1080 mmol, 2 eq) and tert-butyl 4-aminopiperidine-1-carboxylate (114 g, 570 mmol, 1.05 eq) to a suspension of 5,7-dichloro-3-isopropyl-pyrazolo[1,5-a]pyrimidine (130 g, 542 mmol) in 2-propanol (1.0 L) at 23° C. and stir the mixture for 18 hours. filter, wash the solid with MTBE (200 mL), and dry to obtain tert-butyl 4-[(5-chloro-3-isopropyl-pyrazolo[1,5-a]pyrimidin-7-yl)amino]piperidine-1-carboxylate (182 g, 85% yield) as a yellow solid. ES/MS m/z ($^{35}$Cl/$^{37}$Cl) 394/396 (M+H). $^1$H NMR (d$_6$-DMSO) δ 1.28 (d, 6H), 1.42 (s, 9H), 1.61 (m, 2H), 1.83 (m, 2H), 2.87 (m, 1H), 3.10 (dq, 1H), 3.32 (m, 1H), 3.85 (m, 1H), 3.98 (m, 2H), 6.34 (s, 1H), 8.01 (s, 1H), 8.07 (d, 1H).

Preparation 4

Synthesis of Tert-Butyl 4-[tert-butoxycarbonyl-(5-chloro-3-isopropyl-pyrazolo[1,5-a]pyrimidin-7-yl)amino]piperidine-1-carboxylate

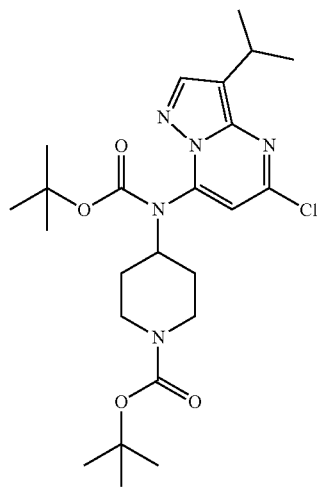 [SMILES: CC(C)c1cnn2c(N(C(=O)OC(C)(C)C)C3CCN(C(=O)OC(C)(C)C)CC3)cc(Cl)nc12]

Add N,N-diisopropylethylamine (69.1 mL, 51.2 g, 396 mmol, 1 eq), 4-dimethylaminopyridine (4.84 g, 39.6 mmol, 0.1 eq), and di-tert-butyl dicarbonate (200 mL, 190 g, 871 mmol, 2.2 eq) to a solution of tert-butyl 4-[(5-chloro-3-isopropyl-pyrazolo[1,5-a]pyrimidin-7-yl)amino]piperidine-1-carboxylate (156 g, 396 mmol) in THF (936 mL) at 23° C., and heat the mixture at 50° C. (internal temperature) for 21 hours. Cool to 23° C. and concentrate in vacuo to obtain tert-butyl 4-[tert-butoxycarbonyl-(5-chloro-3-isopropyl-pyrazolo[1,5-a]pyrimidin-7-yl)amino]piperidine-1-carboxylate (195 g, 99%) as an orange solid. ES/MS m/z ($^{35}$Cl/$^{37}$Cl) 438/440 (M+H−56). $^1$H NMR (d$_6$-DMSO) δ 1.20 (s, 9H), 1.31 (d, 6H), 1.35 (s, 9H), 1.46 (m, 2H), 1.88 (m, 2H), 2.75 (m, 1H), 3.19 (dq, 1H), 3.32 (m, 1H), 3.95 (m, 1H), 4.18 (m, 2H), 7.20 (s, 1H), 8.19 (s, 1H).

Alternative Synthesis of Tert-Butyl 4-[tert-butoxycarbonyl-(5-chloro-3-isopropyl-pyrazolo[1,5-a]pyrimidin-7-yl)amino]piperidine-1-carboxylate Add tert-butyl 4-aminopiperidine-1-carboxylate (2.8 g, 14 mmol) to a solution of 5,7-dichloro-3-isopropyl-pyrazolo[1,5-a]pyrimidine (3.1 g, 13 mmol) in ethanol (32 mL). Heat at 80° C. After 18 hours, cool to RT and concentrate under reduced pressure. Purify the residue by flash chromatography (silica gel), eluting with ethyl acetate:DCM to provide tert-butyl 4-[tert-butoxycarbonyl-(5-chloro-3-isopropyl-pyrazolo[1,5-a]pyrimidin-7-yl)amino]piperidine-1-carboxylate as a white solid. Mass spectrum (m/e): 394,396 (M+1) Add tert-butoxycarbonyl tert-butyl carbonate (1.14 g, 5.22 mmol) to a solution of tert-butyl 4-[(5-chloro-3-isopropyl-pyrazolo[1,5-a]pyrimidin-7-yl)amino]piperidine-1-carboxylate (940 mg, 2.386 mmol) and 4-dimethylaminopyridine (290 mg, 2.33 mmol) in THF (7 mL). Heat the mixture at 60° C. After 30 minutes, cool to RT and concentrate under reduced pressure. Purify the residue by flash chromatography (silica gel), eluting with DCM to provide tert-butyl 4-[tert-butoxycarbonyl-(5-chloro-3-isopropyl-pyrazolo[1,5-a]pyrimidin-7-yl)amino]piperidine-1-carboxylate (1.1 g) as a yellowish oil. Mass spectrum (m/z): 438 (M-t-Bu). $^1$H NMR (400.13 MHz, d$_6$-DMSO): 8.19 (s, 1H), 7.20 (s, 1H), 5.76 (s, 1H), 4.17 (m, 1H), 3.95 (m, 2H), 3.19 (m, 1H), 1.87 (m, 2H), 1.47 (m, 2H), 1.35 (s, 9H), 1-31 (d, 6H), 1.19 (s, 9H).

Preparation 5

Synthesis of Tert-Butyl 4-[tert-butoxycarbonyl-(3-isopropyl-5-methyl-pyrazolo[1,5-a]pyrimidin-7-yl)amino]piperidine-1-carboxylate

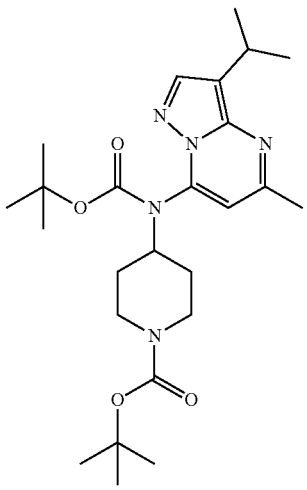 [SMILES: Cc1cc(N(C(=O)OC(C)(C)C)C2CCN(C(=O)OC(C)(C)C)CC2)n2ncc(C(C)C)c2n1]

Add [1,1'-bis(diphenylphosphino)ferrocene]dichloropalladium (II) DCM adduct (15.7 g, 19.3 mmol, 0.05 eq), potassium phosphate tribasic (245 g, 1160 mmol, 3 eq), and 2,4,6-trimethyl-1,3,5,2,4,6-trioxatriborinane (50 mass % in THF, 75.3 mL, 67.6 g, 270 mmol, 0.7 eq) to a solution of tert-butyl 4-[tert-butoxycarbonyl-(5-chloro-3-isopropyl-pyrazolo[1,5-a]pyrimidin-7-yl)amino]piperidine-1-carboxylate (190 g, 385 mmol) in 1,4-dioxane (1.5 L) at 90° C. (internal temperature). After 5 days, cool to 23° C., filter through a pad of diatomaceous earth, and rinse the solid with THF (3×250 mL). Treat combined filtrates at 23° C. with SiliaMetS® Thiol resin (40-63 μm; loading=1.46 mmol/g; 320 g, 467 mmol), and heat to 65° C. for 18 hours. Cool to 23° C., filter, and wash resin with DCM (2×250 mL). Concentrate combined filtrates in vacuo, dissolve the residue in MTBE (1 mL), wash with water (200 mL), dry (MgSO$_4$), and concentrate in vacuo to obtain tert-butyl 4-[tert-butoxycarbonyl-(3-isopropyl-5-methyl-pyrazolo[1,5-a]pyrimidin-7-yl)amino]piperidine-1-carboxylate (182 g, 100%) as a brown solid. ES/MS m/z 474 (M+H).

Preparation 6

Synthesis of 3-isopropyl-5-methyl-N-(4-piperidyl)pyrazolo[1,5-a]pyrimidin-7-amine Dihydrochloride

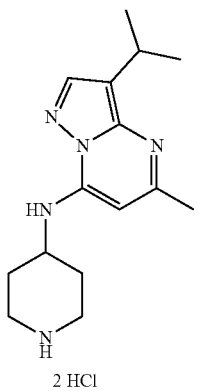 [SMILES: Cc1cc(NC2CCNCC2)n2ncc(C(C)C)c2n1]

2 HCl

Add hydrochloric acid in 2-propanol (5.50 mol/L, 349 mL, 1920 mmol, 5 eq) to a suspension of tert-butyl 4-[tert-butoxycarbonyl-(3-isopropyl-5-methyl-pyrazolo[1,5-a]pyrimidin-7-yl)amino]piperidine-1-carboxylate (182 g, 384 mmol) in 2-propanol (1.4 L) at 23° C., and heat the mixture to 70° C. (internal temperature) for 3 hours. Cool to 23° C., filter, wash the solid with MTBE (2×200 mL) and dry to obtain 3-isopropyl-5-methyl-N-(4-piperidyl)pyrazolo[1,5-a]pyrimidin-7-amine dihydrochloride (95 g, 71% yield) as a yellow solid. Combine mother liquors, dilute with MTBE (2 L), filter, wash the solid with MTBE (2×50 mL), and dry to obtain additional material (8.42 g, 15% yield). ES/MS m/z 274 (M+H). $^1$H NMR (d$_6$-DMSO) δ 1.28 (d, 6H), 2.04 (m, 4H), 2.61 (s, 3H), 3.00 (m, 2H), 3.40 (m, 3H), 4.16 (m, 2H), 6.68 (s, 1H), 8.30 (s, 1H), 8.80 (m, 1H), 9.21 (m, 1H), 9.86 (m, 1H).

Alternative synthesis of 3-isopropyl-5-methyl-N-(4-piperidyl)pyrazolo[1,5-a]pyrimidin-7-amine dihydrochloride Dissolve 7-chloro-3-isopropyl-5-methylpyrazolo[1,5-a]pyrimidine (2.1 kg, 10.0 mol) and diisopropylethylamine (4.18 L, 2.4 eq) in isopropanol (16.8 L, 8 mL/g). Charge tert-butyl 4-aminopiperidine-1-carboxylate (2.6 kg, 1.3 eq.) to the reaction mixture and heat to 75-80° C. for 16 hours. Cool reaction mixture to 5-10° C. and add a 4 M solution of hydrochloric acid in isopropanol (17.5 L, 7.0 eq). Heat to 40-45° C. for 4 hours. Cool to 25-30° C. and filter the mixture to afford the title compound (2.25 kg, 72.7% yield). Material was used in next step without further purification. $^1$H NMR (500 MHz, D$_2$O) δ 8.16 (s, 1H), 6.45 (s, 1H), 4.29-4.26 (m, 1H), 3.63 (d, J=15.0 Hz, 2H), 3.26-3.12 (m, 3H), 2.64 (s, 3H), 2.40 (d, J=15.0 Hz, 2H), 2.08 (dd, J=10.0, 25.0 Hz, 2H), 1.31 (d, J=5.0 Hz, 6H).

Alternative Synthesis of 3-isopropyl-5-methyl-N-(4-piperidyl)pyrazolo[1,5-a]pyrimidin-7-amine as Free Base Add 1,4-dioxane (15 mL) to a mixture of tert-butyl 4-[tert-butoxycarbonyl-(5-chloro-3-isopropyl-pyrazolo[1,5-a]pyrimidin-7-yl)amino]piperidine-1-carboxylate (689 mg, 1.39 mmol), 2,4,6-trimethyl-1,3,5,2,4,6-trioxatriborinane (350 mg, 2.79 mmol) and potassium phosphate tribasic (1.2 g, 5.5 mmol). Bubble N$_2$ on to the solution for 5 minutes. Add [1,1'-bis(diphenylphosphino)ferrocene]dichloropalladium(II) DCM adduct (60 mg, 0.072 mmol). Heat at 110° C. After, 1.5 hours add more [1,1-bis(diphenylphosphino)ferrocene]dichloropalladium(II) (60 mg, 0.072 mmol) and heat at 100° C. After 18 hours, cool to RT, filter the mixture through a pad of filter cell, rinse with ethyl acetate and concentrate under reduced pressure. Purify the residue by flash chromatography (silica gel), eluting with ethyl acetate and DCM to provide tert-butyl 4-[tert-butoxycarbonyl-(3-isopropyl-5-methyl-pyrazolo[1,5-a]pyrimidin-7-yl)amino]piperidine-1-carboxylate (537 mg, 1.077 mmol) as an orangeish oil. Mass spectrum (m/z): 474 (M+1).

Add trifluoroacetic acid (2.5 mL, 33 mmol) dropwise to a solution of tert-butyl 4-[tert-butoxycarbonyl-(3-isopropyl-5-methyl-pyrazolo[1,5-a]pyrimidin-7-yl)amino]piperidine-1-carboxylate (537 mg, 1.077 mmol) in DCM (12 mL). Stir at RT. After 2 hours, concentrate the mixture under reduce pressure. Purify the residue by SCX-2 cartridge elution with 10% DCM:MeOH then MeOH (2 N NH$_3$). Concentrate the basic fraction under reduced pressure to provide 3-isopropyl-5-methyl-N-(4-piperidyl)pyrazolo[1,5-a]pyrimidin-7-amine (345 mg, 1.199 mmol) as a brownish solid. Mass spectrum (m/z): 274 (M+1). $^1$H NMR (400.13 MHz, DMSO): 7.82 (s, 1H), 7.23 (d, 1H), 6.08 (s, 1H), 3.58 (m, 1H), 3.12 (m, 1H), 2.97 (m, 2H), 2.58 (m, 2H), 2.39 (s, 3H), 2.10 (m, 2H), 1.28 (d, 6H).

Preparation 7

Synthesis of [(3S)-1-tert-butoxycarbonylpyrrolidin-3-yl] 4-[(3-isopropyl-5-methyl-pyrazolo[1,5-a]pyrimidin-7-yl)amino]piperidine-1-carboxylate

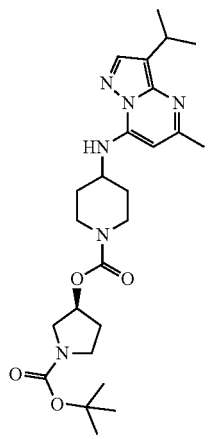 [SMILES: Cc1cc(NC2CCN(C(=O)O[C@H]3CCN(C(=O)OC(C)(C)C)C3)CC2)n2ncc(C(C)C)c2n1]

Add phosgene (20 mass % in toluene, 348 mL, 485 g, 981 mmol, 2.4 eq) to a solution of tert-butyl (3S)-3-hydroxypyrrolidine-1-carboxylate (76.5 g, 409 mmol) in THF (765 mL) placed in a 3 neck RBF connected to a scrubber trap bottle containing 32% aqueous NH$_4$OH, at 23° C. for 1 hour. Bubble N$_2$ through the mixture for 30 minutes, and concentrate in vacuo. Dissolve the residue in DCM (757 mL), cool to 0° C. (internal temperature), and add (slow addition over 7 minutes) a suspension of 3-isopropyl-5-methyl-N-(4-piperidyl)pyrazolo[1,5-a]pyrimidin-7-amine dihydrochloride (94.6 g, 273.2 mmol) in DCM (756.8 mL), previously treated with triethylamine (228 mL, 166 g, 1639 mmol, 6 eq). Remove the cooling bath after addition, and quench the reaction after 30 minutes with 35% aqueous HCl (20 mL) and 1 M aqueous HCl (300 mL) (final pH=7). Separate the organic layer, wash with water (300 mL) and saturated aqueous NaCl (300 mL), dry (MgSO$_4$), and concentrated in vacuo. Dissolve the residue (ca. 180 g) in DCM (1.5 L), add SiliaMetS® Thiol resin (40-63 μm; loading=1.46 mmol/g; 10 g, 14.6 mmol, 140 eq based on Pd content) at 23° C., and then heat the mixture to 40° C. for 2 hours. Filter, rinse the resin with DCM (2×10 mL), and concentrate combined filtrates in vacuo to obtain [(3S)-1-tert-butoxycarbonylpyrrolidin-3-yl] 4-[(3-isopropyl-5-methyl-pyrazolo[1,5-a]pyrimidin-7-yl)amino]piperidine-1-carboxylate (129 g, 97%) as a yellow solid. ES/MS m/z 487 (M+H). $^1$H NMR (d$_6$-DMSO) δ 1.28 (d, 6H), 1.40 (s, 9H), 1.65 (m, 2H), 1.88 (m, 2H), 1.96 (m, 1H), 2.07 (m, 1H), 2.46 (s, 3H), 2.90 (m, 2H), 3.31 (m, 5H), 3.89 (m, 1H), 4.02 (m, 2H), 5.10 (m, 1H), 6.32 (s, 1H), 8.01 (s, 1H).

Alternative Synthesis of [(3S)-1-tert-butoxycarbonylpyrrolidin-3-yl] 4-[(3-isopropyl-5-methyl-pyrazolo[1,5-a]pyrimidin-7-yl)amino]piperidine-1-carboxylate Dissolve tert-butyl (3S)-3-hydroxypyrrolidine-1-carboxylate (438 g, 1.3 eq.) in ACN (4.4 L, 10.0 mL/g) at 15-30° C. Add triethylamine (595 mL, 4.5 eq.) followed by 4-nitrophenyl chloroformate (490 g, 1.4 eq.) at 15-30° C. Heat to 35-40° C. and stir mixture for 4 hours. Cool to 15-25° C. and add 3-isopropyl-5-methyl-N-(piperidin-4-yl)pyrazolo[1,5-a]pyrimidin-7-amine (500 g, 1.8 mol). Stir at 15-30° C. for 5 hours. Concentrate under reduced pressure. Add 2-methyltetrahydrofuran (4.4 L, 10.0 mL/g), stir, and filter. Wash filtrate sequentially with 2 M NaOH (1.1 L, 2.5 mL/g, 4 times) and saturated aqueous NaCl (4.4 L, 10.0 mL/g). Dry over Na$_2$SO$_4$, filter, and concentrate under reduced pressure. Add isopropyl alcohol (2.2 L, 5 mL/g) to obtain a solution of title compound (660 g, 75.4% yield).

Preparation 8

Synthesis of [(3S)-pyrrolidin-3-yl] 4-[(3-isopropyl-5-methyl-pyrazolo[1,5-a]pyrimidin-7-yl)amino]piperidine-1-carboxylate

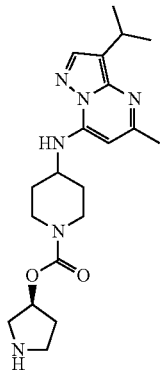 [SMILES: Cc1cc(NC2CCN(C(=O)O[C@H]3CCNC3)CC2)n2ncc(C(C)C)c2n1]

Add hydrochloric acid in 2-propanol (5.50 mol/L, 217 mL, 1190 mmol, 5 eq) to a suspension of [(3S)-1-tert-butoxycarbonylpyrrolidin-3-yl] 4-[(3-isopropyl-5-methyl-pyrazolo[1,5-a]pyrimidin-7-yl)amino]piperidine-1-carboxylate (116 g, 239 mmol) in 2-propanol (755 mL) at 23° C., and heat the mixture to 70° C. for 90 minutes. Cool to 23° C., and concentrate in vacuo. Suspend the residue in DCM (1.5 L), add 1 M aq. NaOH (400 mL) and 50% aq. NaOH (100 mL). Stir for 15 minutes. Separate the organic phase, dry (MgSO$_4$), and concentrate in vacuo. Suspend the residue (ca. 131 g) in MTBE/hexane (2:1, 900 mL), and stir the mixture for 18 hours. Filter, wash the filtered solid with hexane (2×100 mL), and dry to obtain [(3S)-pyrrolidin-3-yl] 4-[(3-isopropyl-5-methyl-pyrazolo[1,5-a]pyrimidin-7-yl)amino]piperidine-1-carboxylate (82.7 g, 90% yield) as a yellow solid. ES/MS m/z 387 (M+H). $^1$H NMR (d$_6$-DMSO) δ 1.28 (d, 6H), 1.60 (m, 3H), 1.88 (m, 3H), 2.40 (s, 3H), 2.75 (m, 2H), 2.91 (m, 4H), 3.13 (dq, 1H), 3.78 (m, 1H), 4.02 (m, 2H), 5.10 (m, 1H), 6.14 (s, 1H), 7.41 (d, 1H), 7.87 (s, 1H).

Alternative Synthesis of [(3S)-pyrrolidin-3-yl] 4-[(3-isopropyl-5-methyl-pyrazolo[1,5-a]pyrimidin-7-yl)amino]piperidine-1-carboxylate Add 5.5 M hydrochloric acid in isopropyl alcohol (8.4 L, 5.0 mL/g) to isopropyl alcohol solution containing (S)-1-(tert-butoxycarbonyl)pyrrolidin-3-yl 4-((3-isopropyl-5-methylpyrazolo[1,5-a]pyrimidin-7-yl)amino)piperidine-1-carboxylate (819 g) at 20-30° C. Heat reaction mixture to 50-60° C. for 5 hours. Cool to 30-35° C., add MTBE (8.2 L, 10 mL/g) and stir for 1 hour. Filter, add wet cake to aqueous sodium hydroxide (3.0 equiv) at 0-5° C. and stir for 30 minutes. Add 2-methyltetrahydrofuran (8.2 L, 10.0 mL/g) and stir. Extract organic phase and wash with saturated aqueous NaCl. Dry over sodium sulfate, filter, and concentrate under reduced pressure to 1-2 volumes. Add MTBE (2.46 L, 3 mL/g) and stir for 3 hours. Filtration affords the title compound (550 g). $^1$H NMR (400 MHz, CDCl$_3$) δ 7.82 (s, 1H), 6.12 (d, J=8.1 Hz, 1H), 5.78 (s, 1H), 5.27-5.13 (m, 1H), 4.26-4.01 (m, 2H), 3.74-3.59 (m, 1H), 3.36-3.23 (m, 1H), 3.14-2.98 (m, 5H), 2.90 (ddd, J=11.1, 8.4, 5.4 Hz, 1H), 2.52 (s, 3H), 2.18-2.00 (m, 3H), 1.87 (dd, J=12.6, 6.4 Hz, 1H), 1.76 (s, 1H), 1.66-1.52 (m, 2H), 1.34 (d, J=6.9 Hz, 6H).

Alternative Synthesis of [(3S)-pyrrolidin-3-yl] 4-[(3-isopropyl-5-methyl-pyrazolo[1,5-a]pyrimidin-7-yl)amino]piperidine-1-carboxylate Add phosgene (1.14 mL, 20 mass % in toluene, 3.20 mmol) to a cold (0° C.) solution of tert-butyl (3S)-3-hydroxypyrrolidine-1-carboxylate (500 mg, 2.67 mmol) and TEA (0.37 mL, 2.6 mmol) in THF (13 mL). Remove the cold bath and stir the mixture at RT. After 30 minutes, concentrate the mixture under reduced pressure and dissolve the residue in DCM (11 mL). Add this solution to a solution of 3-isopropyl-5-methyl-N-(4-piperidyl)pyrazolo[1,5-a]pyrimidin-7-amine (C, 365 mg, 100 mass %, 0.365 g) and TEA (0.3 mL) in DCM (11 mL). Stir the mixture at RT. After 10 minutes, add saturated aqueous NaHCO$_3$ solution and extract with more DCM. Combine the organic layers and wash with saturated aqueous NaCl, dry over magnesium sulfate, filter, and concentrate under reduced pressure to give a residue. Purify the residue by flash chromatography (silica gel), eluting with DCM:MeOH to provide [(3S)-1-tert-butoxycarbonylpyrrolidin-3-yl] 4-[(3-isopropyl-5-methyl-pyrazolo[1,5-a]pyrimidin-7-yl)amino]piperidine-1-carboxylate (671 mg) as a yellowish oil. Mass spectrum (m/z): 487 (M+1).

Add dropwise trifluoroacetic acid (2 mL, 26.45 mmol) to a solution of [(3S)-1-tert-butoxycarbonylpyrrolidin-3-yl] 4-[(3-isopropyl-5-methyl-pyrazolo[1,5-a]pyrimidin-7-yl)

amino]piperidine-1-carboxylate (671 mg, 1.269 mmol) in DCM (12 mL). Stir at RT. After 18 hours, concentrate the mixture under reduced pressure. Dissolve the residue in DCM and wash the organic phase with 10% K$_2$CO$_3$ aqueous solution. Dry the organic phase over magnesium sulfate, filter and concentrate under reduced pressure to provide [(3S)-pyrrolidin-3-yl] 4-[(3-isopropyl-5-methyl-pyrazolo[1,5-a]pyrimidin-7-yl)amino]piperidine-1-carboxylate (274 mg, 0.6593 mmol) as a white foam. Mass spectrum (m/z): 387 (M+1). $^1$H NMR (400.13 MHz, d$_6$-DMSO): 7.87 (s, 1H), 7.42 (d, J=9.0 Hz, 1H), 6.13 (s, 1H), 5.00 (ddd, J=9.0, 5.2, 2.5 Hz, 1H), 4.02 (m, 2H), 3.77 (m, 1H), 3.13 (m, 1H), 2.89 (m, 4H), 2.72 (m, 2H), 2.40 (s, 3H), 1.87 (dd, J=6.8, 14.1 Hz, 2H), 1.63 (m, 3H), 1.28 (d, J=6.8 Hz, 6H).

Preparation 9

Synthesis of [(3R)-pyrrolidin-3-yl] 4-[(3-isopropyl-5-methyl-pyrazolo[1,5-a]pyrimidin-7-yl)amino]piperidine-1-carboxylate

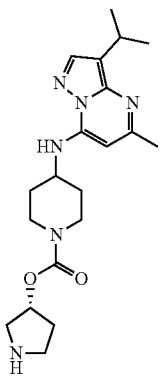 [SMILES: Cc1cc(NC2CCN(C(=O)O[C@@H]3CCNC3)CC2)n2ncc(C(C)C)c2n1]

Add phosene (1.14 mL, 20 mass % in toluene, 3.20 mmol) to a cold (0° C.) solution of tert-butyl (3R)-3-hydroxypyrrolidine-1-carboxylate (500 mg, 2.67 mmol) and TEA (0.37 mL, 2.6 mmol) in THF (13 mL). Remove the cold bath and stir the mixture at RT.

After 30 minutes, concentrate the mixture under reduced pressure and dissolve the residue in DCM (11 mL). Add this solution to a solution of 3-isopropyl-5-methyl-N-(4-piperidyl)pyrazolo[1,5-a]pyrimidin-7-amine (365 mg, 100 mass %, 0.365 g) and TEA (0.3 mL) in DCM (11 mL). Stir the mixture at RT. After 10 minutes, add saturated aqueous NaHCO$_3$ solution and extract with more DCM. Combine the organic layers and wash with saturated aqueous NaCl dry over magnesium sulfate, filter, and concentrate under reduced pressure to give a residue. Purify the residue by flash chromatography (silica gel), eluting with hexane:ethyl acetate to provide [(3R)-1-tert-butoxycarbonylpyrrolidin-3-yl] 4-[(3-isopropyl-5-methyl-pyrazolo[1,5-a]pyrimidin-7-yl)amino]piperidine-1-carboxylate (350 mg) as a yellowish oil. Mass spectrum (m/z): 487 (M+1).

Add dropwise trifluoroacetic acid (0.8 mL, 0.72 mmol) to a solution of [(3R)-1-tert-butoxycarbonylpyrrolidin-3-yl] 4-[(3-isopropyl-5-methyl-pyrazolo[1,5-a]pyrimidin-7-yl)amino]piperidine-1-carboxylate (350 mg, 0.72 mmol) in DCM (7 mL). Stir at RT. After 45 minutes, concentrate the mixture under reduced pressure. Purify the residue by SCX-2 cartridge elution with 10% DCM:MeOH then MeOH (2 N NH$_3$). Concentrate the basic fraction under reduced pressure to provide [(3R)-pyrrolidin-3-yl] 4-[(3-isopropyl-5-methyl-pyrazolo[1,5-a]pyrimidin-7-yl)amino]piperidine-1-carboxylate (246 mg) as a brownish solid. Mass spectrum (m/z): 387 (M+1).

Preparation 10

Synthesis of 3-isopropyl-5-methyl-4H-pyrazolo[1,5-a]pyrimidin-7-one

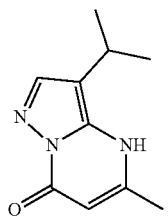

Dissolve 4-isopropyl-1H-pyrazol-5-amine (2.2 kg, 17.6 mol) and ethyl acetoacetate (2.86 kg, 1.25 eq.) into acetic acid (17.6 L, 8.0 mL/g). Heat the mixture to 110-115° C. and then cool to 35-40° C. Add heptane and MTBE (44 L, 20 mL/g, 5/1 ratio). Filter and rinse the solid with-heptane (4.4 L, 2 mL/g) to give the title compound (2.28 kg, 85.5% yield). $^1$H NMR (500 MHz, DMSO) δ 11.81 (s, 1H), 7.77 (s, 1H), 5.50 (s, 1H), 3.08-3.05 (m, 1H), 2.31 (s, 3H), 1.22 (d, J=5.0 Hz, 6H).

Preparation 11

Synthesis of 7-chloro-3-isopropyl-5-methylpyrazolo[1,5-a]pyrimidine

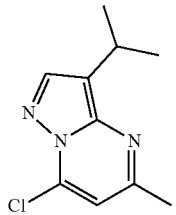

Dissolve 3-isopropyl-5-methyl-4H-pyrazolo[1,5-a]pyrimidin-7-one (2.1 kg, 11.0 mol) and N,N-dimethylaniline (0.86 kg, 0.65 eq.) in ACN (8.4 L, 4 mL/g). Heat the reaction to 50-55° C. and add POCl$_3$ (4.2 kg, 2.5 eq.) dropwise. Adjust temperature to 60-65° C. and stir mixture for 9 hours. Cool mixture to 25-30° C. and pour into 2M potassium phosphate buffer (pH=8.0, 42 L, 20 mL/g). Add MTBE (23.9 L, 11.4 mL/g) and extract the organic phase. Wash organic phase sequentially with 20% citric acid solution (4.2 L, 2.0 mL/g) twice, 10% aqueous solution of NaHCO$_3$ (10.5 L, 5.0 mL/g) and saturated aqueous NaCl (10.5 L, 5.0 mL/g). Dry the organic phase over Na$_2$SO$_4$, filter, and concentrate under reduced pressure to provide the title compound (1.8 kg, 78% yield). $^1$H NMR (400 MHz, CDCl$_3$) δ 8.02 (s, 1H), 6.75 (s, 1H), 3.27-3.25 (m, 1H), 2.58 (s, 3H), 1.42 (d, J=8.0 Hz, 6H).

Preparation 12

3-isopropyl-5-methyl-N-(4-piperidyl)pyrazolo[1,5-a]pyrimidin-7-amine

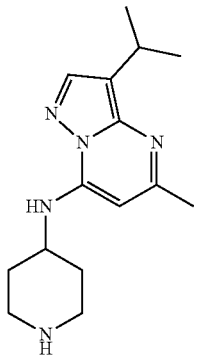 [SMILES: Cc1cc(NC2CCNCC2)n2ncc(C(C)C)c2n1]

Add 3-isopropyl-5-methyl-N-(4-piperidyl)pyrazolo[1,5-a]pyrimidin-7-amine dihydrochloride (2.2 kg, 6.4 mol) to 1 M aqueous solution of sodium hydroxide (19.2 L, 3.0 eq.) at 10-15° C. Stir the reaction mixture for 15-20 minutes then add 2-methyltetrahydrofuran (4.70 L, 10.0 equiv) and stir for 20-25 minutes. Separate the organic phase and wash the aqueous phase with 2-methyltetrahydrofuran (6.6 L, 3.0 mL/g, 3 times). Combine the organic solutions and wash with saturated aqueous NaCl (11 L, 5.0 mL/g). Dry the organic phase over $Na_2SO_4$, filter, and concentrate under reduced pressure. Add MTBE (6.6 L, 3.0 mL/g) and stir for 40 minutes at 25-30° C. Filtration affords the title compound (1.5 kg, 85.7% yield). $^1$H NMR (400 MHz, $CDCl_3$) δ 7.81 (s, 1H), 6.10 (d, J=8.0 Hz 1H), 5.75 (s, 1H), 3.59-3.54 (m, 1H), 3.32-3.28 (m, 1H), 3.22-3.19 (m, 2H), 2.77-2.73 (m, 2H), 2.51 (s, 3H), 2.11 (d, J=8.0 Hz, 2H), 1.56-1.50 (m, 3H), 1.34 (d, J=8.0 Hz, 6H).

Example 1

Synthesis of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (II)*

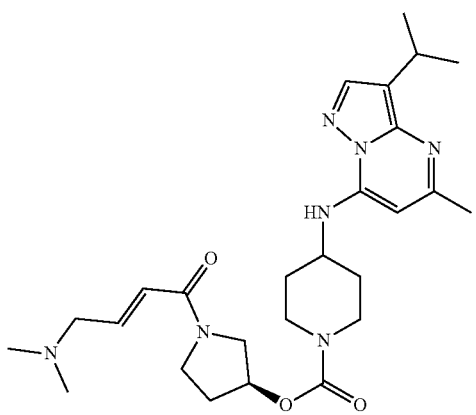

[*Note that as shown here in Example 1, the chiral center has changed orientation and the S enantiomer form is represented differently than as shown above the examples in structure (II).] Add (E)-4-(dimethylamino)but-2-enoic acid hydrochloride (15.0 g, 90.3 mmol, 1.2 eq), N,N-diisopropylethylamine (31.3 mL, 23.4 g, 181 mmol, 2.4 eq), and HATU (42.9 g, 113 mmol, 1.5 eq) to a suspension of [(3S)-pyrrolidin-3-yl] 4-[(3-isopropyl-5-methyl-pyrazolo[1,5-a]pyrimidin-7-yl)amino]piperidine-1-carboxylate (29.1 g, 75.3 mmol) in THF (146 mL) at 23° C., and stir the mixture for 90 minutes. Dilute with phosphate buffer (0.5 M, pH=9, 150 mL), extract with DCM (2×375 mL), dry ($MgSO_4$), and concentrate in vacuo. Purify the resulting residue (ca. 95 g) by chromatography (load residue dissolved in 65 mL of DCM; 330 g of $SiO_2$; eluent: MTBE/7N $NH_3$ in MeOH 0% to 10%; TLC:MTBE/7N $NH_3$ in MeOH 5:1). Dissolve the material (ca. 40 g) in DCM (400 mL), wash with 1 M aq. $K_2HPO_4$ (1 M, 80 mL), dry ($MgSO_4$), and concentrate in vacuo. Purify the residue (ca. 38 g) by chromatography (load residue absorbed in $SiO_2$ (50 g); 330 g of $SiO_2$; eluent: MTBE/7N $NH_3$ in MeOH 0% to 10%) to obtain [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (28.1 g, 75%) as a white solid. ES/MS m/z 498 (M+H). $^1$H NMR ($CD_3OD$) δ 1.33 (d, 6H), 1.64 (m, 2H), 2.10 (m, 2H), 2.18 (m, 1H), 2.26 (m, 1H), 2.29 (s, 6H), 2.50 (s, 3H), 3.11 (m, 2H), 3.18 (dd, 2H), 3.29 (dq, 1H), 3.70 (m, 3H), 3.87 (m, 2H), 4.14 (m, 2H), 5.31 (m, 1H), 6.12 (s, 1H), 6.47 (m, 1H), 6.86 (m, 1H), 7.88 (s, 1H). $[α]_D^{20}$=+49.9° (C=2.0, MeOH). Enantiomeric excess (ee)= 97%. Rt (retention time)=2.79 minutes (UV); LC Column: CHIRALPAK® AS (4.6×150 mm, 5 μm); MeOH+0.2% DMEA; Flow Rate: 1.0 mL/min.

Alternative Synthesis of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate Add N,N-diisopropylethylamine (0.36 mL, 2.1 mmol) to a solution of [(3S)-pyrrolidin-3-yl] 4-[(3-isopropyl-5-methyl-pyrazolo[1,5-a]pyrimidin-7-yl)amino]piperidine-1-carboxylate (170 mg, 0.4091 mmol), (E)-4-(dimethylamino)but-2-enoic acid; hydrochloride (135 mg, 0.81512 mmol) and HATU (317 mg, 0.8181 mmol) in N,N-dimethylformamide (4 mL). Stir at RT. After 5 minutes, concentrate the mixture under reduced pressure. Purify the residue by SCX-2 cartridge eluting with 10% DCM:MeOH then MeOH (2N $NH_3$). Concentrate the basic fraction under reduced pressure and purify the residue through ISCO™ reversed-phase Claricep C-series eluting with $NH_4CO_3$ pH 9/ACN to provide [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (129 mg, 0.255 mmol) as a white solid. Mass spectrum (m/z): 498 (M+1). $^1$H NMR (400.13 MHz, MeOD): 7.88 (s, 1H), 6.85 (m, 1H), 6.47 (m, 1H), 6.12 (s, 1H), 3.91-3.52 (m, 5H), 3.13 (m, 1H), 3.03 (m, 2H), 2.94 (m, 1H), 2.39 (s, 3H), 2.15 (s, 6H), 2.06 (m, 1H), 1.88 (d, J=11.5 Hz, 2H), 1.66 (m, 2H), 1.28 (d, J=6.8 Hz, 6H).

Alternative Synthesis of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate Dissolve [(3S)-pyrrolidin-3-yl] 4-[(3-isopropyl-5-methyl-pyrazolo[1,5-a]pyrimidin-7-yl)amino]piperidine-1-carboxylate (550 g, 1.4 mol) in THF (5.5 L, 10.0 mL/g) at 15-30° C. Add (E)-4-(dimethylamino)but-2-enoic acid hydrochloride (278 g, 1.2 eq.) and TEA (1.17 L, 6.0 eq.) at 15-30° C. and stir for 40 minutes. Add 50% propylphosphonic anhydride in EtOAc (1.68 L, 1.2 equiv) at 15-30° C. and stir for 12 hours. Filter and solvent exchange the filtrate with isopropyl acetate under reduced pressure. Add 2 M aqueous NaOH (2.75 L, 5 mL/g) and stir for 20 minutes at 25-30° C. Extract the organic phase and wash with saturated aqueous NaCl (2.75 L, 5 mL/g). Dry over $Na_2SO_4$, filter, and concentrate under reduced pressure. Add heptane (3.85 L, 7 mL/g) and THF (16.5 L, 3 mL/g) at 15-30° C. Stir for 1 hour and filter to afford the title compound (440 g, 63.2% yield).
$^1$H NMR (500 MHz, $CD_3OD$) δ 7.86 (s, 1H), 6.83 (d, J=10.7 Hz, 1H), 6.43 (dd, J=34.3, 14.9 Hz, 1H), 6.08 (s, 1H), 5.26 (d, J=24.2 Hz, 1H), 4.85 (s, 2H), 4.22-4.01 (m, 2H), 3.90-3.76 (m, 2H), 3.61-3.47 (m, 1H), 3.36-3.21 (m, 2H), 3.17-3.11 (m, 2H), 3.12-2.98 (m, 2H), 2.47 (s, 3H), 2.28-2.21 (m, 7H), 2.16-2.00 (m, 3H), 1.68-1.48 (m, 2H), 1.30 (d, J=6.2 Hz, 6H).

Example 2

Synthesis of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hydrochloride

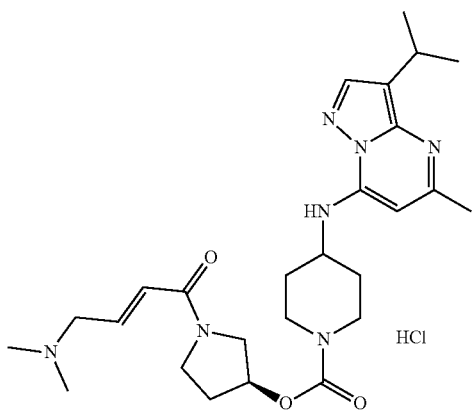

(II)*

[*Note that as shown here in Example 2, the chiral center has changed orientation and the S enantiomer form is represented differently than as shown above the Examples in structure (II).] Add HCl (1 M in EtOAc (0.589 mL, 0.590 g, 0.589 mmol, 1.07 eq) to a solution of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (0.283 g, 0.549 mmol) in acetone (5.5 mL) at 23° C., and stir the mixture for 5 hours. Concentrate in vacuo to obtain [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate hydrochloride (0.244 g, 81%) as a white solid. ES/MS m/z 498 (M+H).
$^1$H NMR ($CD_3OD$) δ 1.34 (d, 6H), 1.66 (m, 2H), 2.11 (m, 2H), 2.20 (m, 1H), 2.30 (m, 1H), 2.54 (s, 3H), 2.90 (s, 6H), 3.12 (m, 2H), 3.28 (dq, 1H), 3.74 (m, 4H), 3.95 (dd, 2H), 4.16 (m, 2H), 4.63 (m, 1H), 5.32 (m, 1H), 6.22 (s, 1H), 6.78 (m, 2H), 7.94 (s, 1H).

Example 3

Synthesis of [(3R)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate

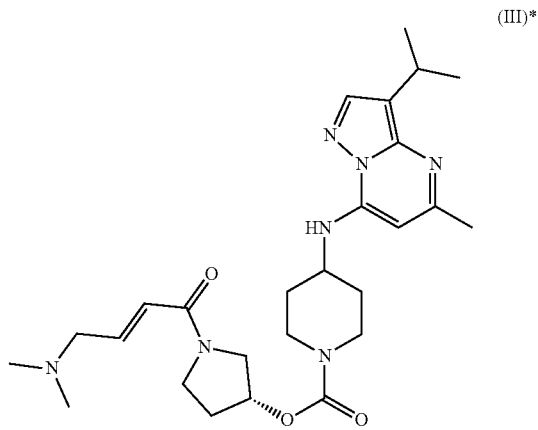

(III)*

[*Note that as shown here in Example 3, the chiral center has changed orientation and the R enantiomer form is represented differently than as shown above the Examples in structure (III).] Add N,N-diisopropylethylamine (0.4 mL, 2.0 mmol) to a solution of [(3R)-pyrrolidin-3-yl] 4-[(3-isopropyl-5-methyl-pyrazolo[1,5-a]pyrimidin-7-yl)amino]piperidine-1-carboxylate (170 mg, 0.43 mmol), (E)-4-(dimethylamino)but-2-enoic acid; hydrochloride (150 mg, 0.90 mmol) and HATU (343 mg, 0.87 mmol) in DMF (4 mL). Stir at RT. After 5 minutes, concentrate the mixture under reduced pressure. Purify the residue by SCX-2 cartridge eluting with 10% DCM:MeOH then MeOH (2 N $NH_3$). Concentrate the basic fraction under reduced pressure and purify the residue through ISCO reversed-phase Claricep C-series eluting with $NH_4CO_3$ pH 9/ACN to provide [(3R)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (188 mg) as a white solid. Mass spectrum (m/z): 498 (M+1).
$^1$H NMR (400.21 MHz, DMSO): 7.86 (s, 1H), 7.41 (m, 1H), 6.63 (m, 1H), 6.37 (m, 1H), 6.13 (s, 1H), 5.16 (m, 1H), 4.09-3.92 (m, 2H), 3.78 (m, 2H), 3.56 (m, 2H), 3.13 (m, 1H), 3.03 (m, 2H), 2.93 (m, 1H), 2.39 (s, 3H), 2.14 (s, 6H), 2.06 (m, 1H) 1.88 (m, 2H), 1.60 (m, 2H), 1.28 (d, J=6.8 Hz, 6H).

Example 4

Synthesis of Crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate Hemi-Edisylate Hydrate

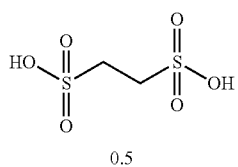

0.5

-continued

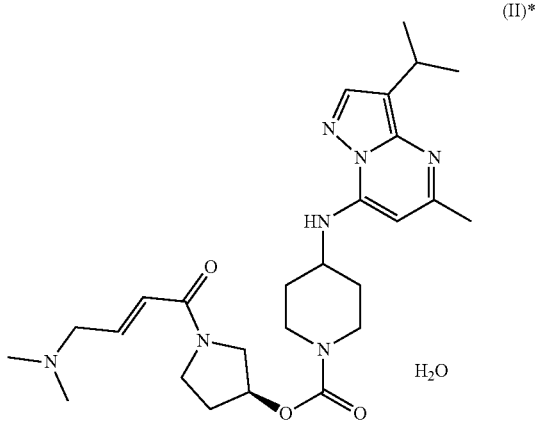

(II)*

[*Note that as shown here in Example 4, the chiral center has changed orientation and the S enantiomer form is represented differently than as shown above the Examples in structure (II).] Place 2.0 g of [(3S)-1-[(E)-4-(dimethyl-amino)but-2-enoyl]pyrrolidin-3-yl] 4-[(3-isopropyl-5-methyl-pyrazolo[1,5-a]pyrimidin-7-yl)amino]piperidine-1-carboxylate in 8 mL of acetone while magnetic stirring at room temperature. In a separate vial, dissolve 505 mg of 1,2-ethanedisulfonic acid hydrate in 6 mL of acetone. Add the acid solution to the freebase solution and mix at RT. Stir the sample so that mixing is thorough, adding additional solvent to thin the slurry if necessary. Slurry the suspension overnight at 50° C. After stirring overnight, cool the remaining thick slurry of white solid to 20° C. Isolate the solids by vacuum filtration on filter paper and dry the resulting cake of white solid in place on the filter (2.1 g, 88% yield).

Obtain the XRD patterns of the crystalline solid on a Bruker D4 Endeavor X-ray powder diffractometer, equipped with a CuKα source λ=1.54060 Å) and a Vantec detector, operating at 35 kV and 50 mA. Scan the sample between 4 and 40° in 2θ, with a step size of 0.008° in 2θ and a scan rate of 0.5 seconds/step, and with 0.6 mm divergence, 5.28 fixed anti-scatter, and 9.5 mm detector slits. Pack the dry powder on a quartz sample holder and obtain a smooth surface using a glass slide. Collect the crystal form diffraction patterns at room temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. Adjust the crystal form diffraction patterns, collected at room temperature and relative humidity, based on NIST 675 standard peaks at 8.853 and 26.774 degrees 2-theta.

A prepared sample of the crystalline hemi-edisylate hydrate is characterized by an XRD pattern using CuKα radiation as having diffraction peaks (2-theta values) as described in the table below, and in particular having a peak at 18.5° in combination with one or more peaks selected from the group consisting of 21.5°, 16.7°, and 15.2°; with a tolerance for the diffraction angles of 0.2 degrees.

X-Ray Powder Diffraction Peaks of the Crystalline Hemi-Edisylate Hydrate

| | Crystalline Hemi-edisylate hydrate | |
|---|---|---|
| Peak | Angle (°2-Theta) +/− 0.2° | Relative Intensity (% of most intense peak) |
| 1 | 7.0 | 14.90% |
| 2 | 10.3 | 36.50% |
| 3 | 12.6 | 14.50% |
| 4 | 15.2 | 47.70% |
| 5 | 16.7 | 58.40% |
| 6 | 18.5 | 100.00% |
| 7 | 19.8 | 16.10% |
| 8 | 21.5 | 63.20% |
| 9 | 23.2 | 17.50% |
| 10 | 24.3 | 10.90% |

Example 5

Synthesis of Crystalline [(3S)-1-[(E)-4-(dimethyl-amino)but-2-enoyl]pyrrolidin-3-yl] 4-[(3-isopropyl-5-methyl-pyrazolo[1,5-a]pyrimidin-7-yl)amino]piperidine-1-carboxylate Besylate

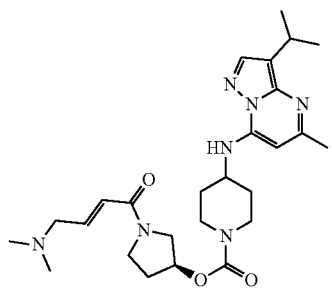

(II)*

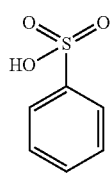

[*Note that as shown here in Example 5, the chiral center has changed orientation and the S enantiomer form is represented differently than as shown above the examples in structure (II).] Place 1998 mg of [(3S)-1-[(E)-4-(dimethyl-amino)but-2-enoyl]pyrrolidin-3-yl] 4-[(3-isopropyl-5- methyl-pyrazolo[1,5-a]pyrimidin-7-yl)amino]piperidine-1-carboxylate in 15 mL of acetone while stirring at 1000 rpm at RT. Add 650 mg of benzenesulfonic acid (dissolved in 5 mL of acetone). Stir the sample at 1000 rpm at RT for one hour, and after some time, the solution clouds, and a thick slurry of white solid results. Isolate the white solid by vacuum filtration on filter paper. Dry the sample in the vacuum oven for 1 hour at 70° C. (2.23 g, 85% yield).

Synthesis of Crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate Besylate Dissolve [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate (440 g, 1.1 mol) in EtOAc (1.4 L) and acetone (357 mL) at 15-30° C. Heat to 50-55° C. Dissolve benzenesulfonic acid monohydrate (156 g, 0.89 eq.) in EtOAc (709 mL) and acetone (166 mL) and add to reaction mixture at 5-10 mL/minutes at 50-55° C. Stir for 1 hour. Cool to 15-30° C. and stir for 12 hours. Filter and dry wet cake under nitrogen to afford title compound (525 g 72.9% yield). 1H NMR (500 MHz, $CD_3OD$) δ 7.89 (s, 1H), 7.85-7.79 (m, 2H), 7.43-7.39 (m, 3H), 6.82-6.66 (m, 2H), 6.15 (s, 1H), 5.27 (d, J=21.5 Hz, 1H), 4.11 (d, J=32.9 Hz, 2H), 3.94-3.79 (m, 4H), 3.33-3.18 (m, 2H), 3.10-2.97 (m, 2H), 2.84 (s, 6H), 2.49 (s, 3H), 2.25-1.94 (m, 5H), 1.68-1.51 (m, 2H), 1.31 (d, J=6.8 Hz, 6H).

Obtain the XRD patterns of the crystalline solid essentially as described in Example 4. A prepared sample of the crystalline besylate is characterized by an XRD pattern using CuKa radiation as having diffraction peaks (2-theta values) as described in the table below, and in particular having a peak at 21.5° in combination with one or more peaks selected from the group consisting of 12.4°, 17.3°, and 15.8°; with a tolerance for the diffraction angles of 0.2 degrees.

X-Ray Powder Diffraction Peaks of the Crystalline Besylate

| | Crystalline Besylate | |
|---|---|---|
| Peak | Angle (°2-Theta) +/− 0.2° | Relative Intensity (% of most intense peak) |
| 1 | 6.3 | 46.30% |
| 2 | 9.5 | 26.30% |
| 3 | 10.7 | 26.30% |
| 4 | 12.4 | 98.70% |
| 5 | 15.8 | 52.00% |
| 6 | 16.5 | 45.20% |
| 7 | 17.3 | 56.60% |
| 8 | 21.5 | 100.00% |
| 9 | 23.4 | 36.80% |
| 10 | 24.9 | 32.10% |

Example 6

Synthesis of Crystalline [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate Hydrochloride

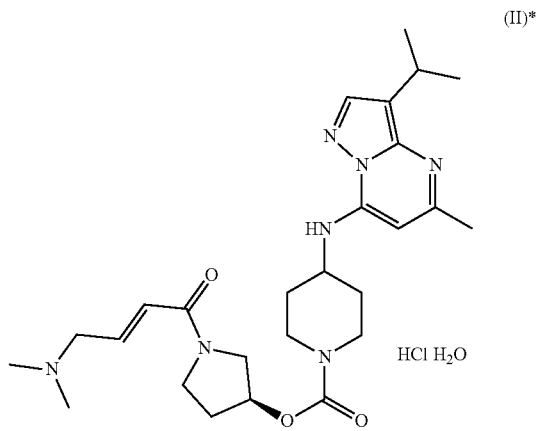

(II)*

[*Note that as shown here in Example 6, the chiral center has changed orientation and the S enantiomer form is represented differently than as shown above the examples in structure (II).] Place 557 mg of [(3S)-1-[(E)-4-(dimethylamino)but-2-enoyl]pyrrolidin-3-yl] 4-[(3-isopropyl-5-methyl-pyrazolo[1,5-a]pyrimidin-7-yl)amino]piperidine-1-carboxylate in 4 mL of acetone while stirring at 1000 rpm at RT. Add 1200 µL of HCl (1M in ethyl acetate, 1.07 eq.). Stir the sample at 1000 rpm overnight to give a thick slurry of white solid. Isolate the white solid by vacuum filtration on filter paper. Dry the resulting cake of white solid in place on the filter under air stream for 10 minutes (385 mg, 64% yield).

Obtain the XRD patterns of the crystalline solid essentially as described in Example 4. A prepared sample of the crystalline hydrochloride hydrate is characterized by an XRD pattern using CuKa radiation as having diffraction peaks (2-theta values) as described in the table below, and in particular having a peak at 18.9° in combination with one or more peaks selected from the group consisting of 5.5°, 15.5°, and 9.7°; with a tolerance for the diffraction angles of 0.2 degrees.

X-Ray Powder Diffraction Peaks of the Crystalline Hydrochloride

| | Crystalline Hydrochloride | |
|---|---|---|
| Peak | Angle (°2-Theta) +/− 0.2° | Relative Intensity (% of most intense peak) |
| 1 | 5.5 | 79.40% |
| 2 | 6.2 | 54.40% |
| 3 | 9.2 | 31.50% |
| 4 | 9.7 | 56.10% |
| 5 | 11.1 | 26.70% |
| 6 | 14.2 | 29.80% |
| 7 | 15.5 | 61.70% |
| 8 | 18.9 | 100.00% |
| 9 | 19.5 | 30.80% |
| 10 | 23.4 | 40.40% |

Biological Assays

The following assays demonstrate that a compound of the invention is an inhibitor of CDK7 activity. The results of the assays also show that a compound of the invention inhibits CDK7 signaling in the cancer cells. Additionally, a compound of the invention inhibits proliferation in cancer cell lines and tumor growth in xenograft tumor model of cancer.

"$IC_{50}$" refers to the concentration of an agent that produces 50% of the maximal inhibitory response possible for that agent or, alternatively, to the concentration of an agent which produces 50% displacement of ligand specific binding to the receptor; Relative $IC_{50}$ values are determined using fluorescence unit by calculating percent inhibition with respect to on-plate "MIN" and "MAX" controls and then fitting the ten-point dose response data to a four-parameter logistic equation.

CDK7 and CDK9 Kinase Activity Assays

The purpose of this assay is to measure the ability of a compound of the invention to inhibit CDK7/CyclinH/Mat1 complex kinase activity. To demonstrate whether compounds included within the present invention exhibit any affinity for CDK7, CDK7 and CDK9, the biochemical assays are performed with no preincubation of the enzyme with the compound or with 3 hours preincubation. Functional assays provide support on whether the compounds of the present invention exhibit the ability to inhibit the CDK7 and CDK9 kinase activities. All ligands, solvents, and reagents employed in the following assays are readily available from commercial sources, or can be readily synthesized by one skilled in the art. The $IC_{50}$ determination for CDK7 and CDK9 are determined as follows.

Biochemical Assay for Inhibition of CDK7/CyclinH/MAT1

The $IC_{50}$ activity of the inhibitor is determined using radiolabel filter binding (FB) assays using the purified human recombinant enzyme in the presence of ATP//[$^{33}$P] ATP and peptide substrate. The ATP concentrations chosen are at or near the enzyme Km for ATP.

Reactions are carried out in 96 well polystyrene plates in a final volume of 25 µL per well. 5 µL of test compound in 20% DMSO, 10 µL of substrate solution (ATP/33PATP and CDK7/9 tide) and 10 µL of enzyme solution are mixed. The substrate solution is prepared to give a final concentration of 100 µM ATP/[$^{33}$P]ATP (NEN 10 µCi/µL, 3000 Ci/mmol) and 250 µM CDK7/9 peptide ((YSPTSPSYSPTSPSYS-PTSPSKKKK) (SEQ ID NO: 1)) diluted in kinase buffer of 4 mM MgCl$_2$, 0.01% TRITON™ X-100, 2 mM DTT and 20 mM HEPES. The enzyme solution is prepared for a final concentration of 1 nM CDK7/CyclinH/Mat1 enzyme [Proqinase 0366-0360-4 Lot 002)] diluted in kinase buffer. Test compounds are serially diluted 1:3 in 20% DMSO to create a 10 point curve at a starting concentration of 20 µM. 20% DMSO buffer alone without test compound is employed as high control (full activity in the absence of any inhibitor), 500 mM EDTA is used to determine the level of background in the absence of enzyme activity (low control). After mixing 5 µL of compounds with 10 µL of enzyme solution the plate is incubated for 0 or 180 minutes at 22° C. After that time the reaction is initiated by the addition of 10 µL substrate solution and incubated for 50 minutes at 22° C. The reaction is terminated by the addition of 80 µL of cold 10% ortophosphoric solution. The Filter Plates (opaque, non-sterile filter plates) are prewashed with 10 µL of 10% orthophosphoric solution to each well. 100 µL of the mixture are transferred to a phosphocellulose filter and incubated at room temperature for 45 minutes. Filter plates are washed with 200 µL 0.5% orthophosphoric acid 3 times on a filter plate processor. Incorporation of 33Pi (counting of "cpm") is determined by adding 80 µL of MICROSCINT™ to each well and read on a counter after an hour. Data is processed through a GENEDATA SCREENER® tool. Data are analyzed using a 4-parameter nonlinear logistic equation (four-parameter logistic concentration-response curve): Y=bot+[(top−bot)/1+(x/IC$_{50}$)slope] where Y=% inhibition, X=concentration yielding y % inhibition, Bottom=minimum value of y attained by curve, Top=maximum value of y attained by curve and Slope=steepness of curve at $IC_{50}$.

% Inh=[(median Max−x/median Max−median Min)]·100

$IC_{50}$: concentration of compound that reduces a given response (ligand binding, enzyme response) by 50%.

The compounds described in Examples 1 and 3 display an $IC_{50}$ of 0.0173 µM and 0.0487 µM in CDK7 without preincubation, respectively. After 3 hours of preincubation of CDK7 enzyme with Examples 1 and 3, they show an $IC_{50}$ of 0.00237 µM and 0.00506 µM, respectively. These data show that both Examples 1 and 3 inhibit CDK7.

Assay for Inhibition of CDK9/CyclinT1 Kinase Activity

The $IC_{50}$ activity of the inhibitor is determined using radiolabel filter binding (FB) assays using the purified human recombinant enzyme in the presence of ATP and peptide substrate. The ATP concentrations chosen are at or near the enzyme Km for ATP. Reactions are carried out in 96 well polystyrene plates in a final volume of 25 µL per well. 5 µL of test compound in 20% DMSO, 10 µL of substrate solution (ATP//[$^{33}$P]ATP and CDK7/9 tide) and 10 µL of enzyme solution are mixed. The substrate solution is prepared to give a final concentration of 100 µM ATP/[$^{33}$P]ATP (NEN 10 uCi/µL, 3000 Ci/mmol) and 200 µM CDK7/9 peptide ((YSPTSPSYSPTSPSYSPTSPSKKKK) (SEQ ID NO: 1)) diluted in kinase buffer of 4 mM MgCl$_2$, 0.0025% TRITON™ X-100, 1.58 mM DTT and 15.80 mM HEPES. The enzyme solution is prepared for a final concentration of 7.5 nM CDK9/cyclinT1 enzyme [Proqinase 0371-0345-1 (Lot 004)] diluted in kinase buffer. Test compounds are serially diluted 1:3 in 20% DMSO to create a 10 point curve at a starting concentration of 20 µM. 20% DMSO buffer alone without test compound is employed as high control (full activity in the absence of any inhibitor), 500 mM EDTA is used to determine the level of background in the absence of enzyme activity (low control). After mixing 5 µL of compounds with 10 µL of enzyme solution the plate is incubated for 0 or 180 minutes at 22° C. After that time the reaction is initiated by the addition of 10 µL substrate solution and incubated for 60 minutes at 22° C. The reaction is terminated by the addition of 80 µL of cold 10% orto-phosphoric solution. Filter plates (opaque, non-sterile filter plates) are prewashed with 10 µL of 10% orthophosphoric solution per well. 100 µL of the mixture are transferred to a phosphocellulose filter and incubate at room temperature for 45 minutes. Filter plates are washed with 200 µL 0.5% orthophosphoric acid 3 times on a filter plate processor. 80 µL of MICROSCINT™ is added to each well and read on a scintillation counter after an hour. Data is processed through a GENEDATA-SCREENER® tool. Data is analyzed using a 4-parameter nonlinear logistic equation (four-parameter logistic concentration-response curve): Y=bot+[(top−bot)/ 1+(x/IC$_{50}$)slope] where Y=% inhibition, X=concentration yielding y % inhibition, Bottom=minimum value of y attained by curve, Top=maximum value of y attained by curve and Slope=steepness of curve at IC$_{50}$. % Inh=[(median Max−x/median Max−median Min)]·100 IC$_{50}$: concentration of compound that reduces a given response (ligand binding, enzyme response) by 50%. IC$_{50}$ relative: concentration giving half the compound's maximum response.

The compounds described in Examples 1 and 3 display an IC$_{50}$ of 5.93 μM and 2.45 μM for CDK9 (3 hours preincubation), respectively. These data show that Examples 1 and 3 do not potently inhibit CDK9 activity.

Taken together, the data from the assays above demonstrate that the compounds of Examples 1 and 3 selectively inhibit CDK7 over CDK9.

CDK7 and CDK9 Cell Mechanistic Assays

The purpose of these assays is to measure the ability of compounds to inhibit CDK7 and CDK9 signaling in cancer cells in vitro.

Phospho-Carboxyl Terminal Domain (Rbp2) (Ser2) p-CTD (S2) Cell Based Acumen Assay HCT116 cells (ATCC CCL-247) are cultured in McCoy's 5A Medium Modified media supplemented with 10% FBS, 1% NaPyr and 1% Pen/Strep and plated (prior to becoming 70% confluent) in 96-well flat-bottom plates at a density of 5,000 cells per well in 100 μL volume. The cells are then incubated overnight in a cell culture incubator (5% $CO_2$, 95% Relative Humidity (RH) and 37° C.) and allowed to attach to the plate. The following morning the cells are dosed with compounds. Compound inhibitors are first solubilized at 60 μM in culture medium containing 0.6% DMSO. Subsequently compound serial dilutions (1:3) are prepared over a 60 μM to 0.003 μM range. Cells are dosed with the addition of 50 μL from serial dilution plate to assay plate containing cells attached with 100 μL of media producing a final DMSO concentration of 0.2% with a final compound concentration dose range between 20 and 0.001 μM. For max point media containing 0.2% of DMSO is used and for min point, a reference compound diluted at 0.83 μM final concentration in the growth media containing 0.2% DMSO is used. After dosing with compounds the cell plates are incubated at 37° C. and 5% $CO_2$ for 4 hours. The growth media is removed carefully and the cells are fixed by adding 100 μL of 4% para-formaldehyde for 30 minutes at RT. Cells are washed once with PBS and incubated with 100 μL of cold MeOH for 15 minutes at RT for cell permeation. Cells are washed twice with PBS (100 μL/each) and blocked with 100 μL/well of 1% BSA/PBS for 30 minutes at RT. 50 μL of 1:1000 primary antibody (Anti-phospho CTD Ser2 Abcam, cat # ab5095-100) dilution in 1% BSA/PBS are added per well, the plates are sealed and incubated overnight at 4° C.

The following day cells are washed three times with PBS (100 μL/well) and incubated with 50 μL/well of secondary antibody (1:2000 dilution, Goat anti-rabbit IgM ALEXA FLUOR™ 488) in PBS for 1 hour at RT. After washing 3× with PBS (100 μL/well), 100 μL of 50 μg/mL RNAase and 1:1000 propidium iodide dilution in PBS are added per well. Plates are sealed and incubated 1 hour at RT on the bench (preserved from light). Plates are analyzed on Acumen on FL2 (mean intensity), and FL3 (total intensity). Fluorescence plates are scanned with ACUMEN EXPLORER™ [Laser-scanning fluorescence microplate cytometer manufactured by TTP LABTECH LTD] to measure anti-phospho-carboxyl terminal domain at Serine 2 (pCTD). Image analysis is based on cellular fluorescent signals for identifying positive cells. pCTD (S2) positive cells are identified by mean intensity at 500-530 above the threshold. Total intensity at 575-640 from propidium iodide/DNA is used to identify individual cells. Assay output is % pCTD positive cells.

The IC$_{50}$ is determined by curve fitting to a four parameter logistic for each output using GENE DATA™. The compounds described in Examples 1 and 3 display a relative IC$_{50}$>20 μM and 3.52 μM for phosphoCTD (S2), respectively. These data show that both Examples 1 and 3 do not potently inhibit CDK9 in the cells.

Phospho-Carboxyl Terminal Domain (Rbp2) (Ser5) p-CTD (S5) Cell Based Acumen Assay HCT116 cells (ATCC CCL-247) are cultured in McCoy's 5A Medium Modified media supplemented with 10% FBS, 1% NaPyr and 1% Pen/Strep and plated (prior to becoming 70% confluent) in 96-well flat-bottom plates at a density of 5,000 cells per well in 100 μL volume. The cells are incubated overnight in a cell culture incubator (5% $CO_2$, 95% Relative Humidity (RH) and 37° C.) and allowed to attach to the plate. The following morning, the cells are dosed with compounds. Compound inhibitors are solubilized at 60 μM in culture medium containing 0.6% DMSO. Subsequently compound serial dilutions (1:3) are prepared over a 60 μM to 0.003 μM range. Cells are dosed with the addition of 50 μL from serial dilution plate to assay plate containing cell attached with 100 μL of media producing a final DMSO concentration of 0.2% with a final compound concentration dose range between 20 and 0.001 μM. For max point media containing 0.2% of DMSO is used and for min point, a reference compound diluted at 0.83 μM final concentration in the growth media containing 0.2% DMSO is used. After dosing with compounds the cell plates are incubated at 37° C. and 5% $CO_2$ for 4 hours. Growth media is removed carefully and the cells are fixed by adding 100 μL of 4% para-formaldehyde for 30 minutes at RT. Cell are washed once with PBS and incubated with 100 μL of cold MeOH for 15 minutes at RT for cell permeation. Again cells are washed twice with PBS (100 μL/each) and blocked with 100 μL/well of 1% BSA/PBS for 30 min at RT. 50 μL of 1:1000 primary antibody (Anti-phosphoCTD Ser5 Bethyl Laboratories cat # A300-655A) dilution in 1% BSA/PBS are added per well, the plates are sealed and incubated overnight at 4° C.

The following day cells are washed three times with PBS (100 μL/well) and incubated with 50 μL/well of secondary antibody (1:2000 dilution, Goat anti-rabbit IgM ALEXA FLUOR™ 488) in PBS for 1 hour at room temperature. After washing 3× with PBS (100 μL/well), 100 μL of 50 μg/mL RNAase (Sigma) and 1:1000 propidium iodide dilution in PBS are added per well. Plates are sealed and incubated for 1 hour at RT on the bench (preserved from light). Plates are analyzed on Acumen on FL2 (mean intensity), and FL3 (total intensity). Fluorescence plates are scanned with ACUMEN EXPLORER™ [Laser-scanning fluorescence microplate cytometer manufactured by TTP LABTECH LTD] to measure anti-phospho-carboxyl terminal domain at Serine 5 (pCTD). Image analysis is based on cellular fluorescent signals for identifying positive cells. pCTD (S5) positive cells are identified by mean intensity at 500-530 above the threshold. Total intensity at 575-640 from propidium iodide/DNA is used to identify individual cells. Assay output is % pCTD positive cells. The $IC_{50}$ is determined by curve fitting to a four parameter logistic for each output using GENE DATA™.

The compounds described in Examples 1 and 3 display a Relative $IC_{50}$ of 0.148 µM and 0.198 µM for pCTD Ser5, respectively. These data show that both Examples 1 and 3 inhibit CDK7 cellular activity.

cMyc Cell Based Acumen Assay

HCT116 cells (ATCC CCL-247) are cultured in McCoy's 5A Medium Modified media supplemented with 10% FBS, 1% NaPyr and 1% Pen/Strep and plated (prior to becoming 70% confluent) in 96-well flat-bottom plates at a density of 5,000 cells per well in 100 µL volume. The cells are then incubated overnight in a cell culture incubator (5% $CO_2$, 95% Relative Humidity (RH) and 37° C.) and allowed to attach to the plate. The following morning the cells are dosed with compounds. Compound inhibitors are solubilized at 60 µM in culture medium containing 0.6% DMSO. Subsequently compound serial dilutions (1:3) are prepared over a 60 µM to 0.003 µM range. Cells are dosed with the addition of 50 µL from serial dilution plate to assay plate containing cell attached with 100 µL of media producing a final DMSO concentration of 0.2% with a final compound concentration dose range between 20 µM and 0.001 µM. For max point media containing 0.2% of DMSO is used and for min point, a reference compound diluted at 0.83 µM final concentration in the growth media containing 0.2% DMSO is used. After dosing with compounds the cell plates are incubated at 37° C. and 5% $CO_2$ for 4 hours. Growth media is removed carefully and the cells are fixed by adding 100 µL of 4% para-formaldehyde for 30 minutes at RT. Cell are washed once with PBS and incubated with 100 µL of cold MeOH for 15 minutes at RT for cell permeation. Again cell are washed twice with PBS (100 µL/each) and blocked with 100 µL/well of 1% BSA/PBS for 30 minutes at RT. 50 µL of 1:1000 primary antibody (Anti-c-Myc antibody [Y69] Abcam cat # ab32072) dilution in 1% BSA/PBS are added per well, the plates sealed and incubated overnight at 4° C. The following day cells are washed three times with PBS (100 µL/well) and incubated with 50 µL/well of secondary antibody (1:2000 dilution, Goat anti-rabbit IgM ALEXA FLUOR™ 488) in PBS for 1 hour at RT. After wash 3× with PBS (100 µL/well), 100 µL of 50 µg/mL RNAase and 1:1000 propidium iodide (Invitrogene) dilution in PBS are added per well. Plates are sealed and incubated for 1 hour at RT on the bench (preserved from light). Plates are analyzed on Acumen on FL2 (mean intensity), and FL3 (total intensity). Fluorescence Plates are scanned with ACUMEN EXPLORER™ [Laser-scanning fluorescence microplate cytometer manufactured by TTP LABTECH LTD] to measure anti-phospho-carboxyl terminal domain at Serine 5 (pCTD). Image analysis is based on cellular fluorescent signals for identifying positive cells. pCTD (S5) positive cells are identified by mean intensity at 500-530 above the threshold. Total intensity at 575-640 from propidium iodide/DNA is used to identify individual cells. Assay output is % pCTD positive cells. The $IC_{50}$ is determined by curve fitting to a four parameter logistic for each output using GENE DATA™.

The compounds described in Examples 1 and 3 display a Relative $IC_{50}$ of 0.0828 µM and 0.0573 µM for cMyc. These data show that both Examples 1 and 3 inhibit the transcription of cMyc in HCT116 cells.

Selectivity Profiling Experiment: Proqinase WT Profiler

Kinase inhibition profile of compound is determined by measuring residual activity values at four concentrations in singlicate in 320 wild-type protein kinase assays. The compounds are tested at 20 µM, 2 µM, 0.2 µM and 0.02 µM in singlicate. The final DMSO concentration in all reaction cocktails (including high and low controls) is 1%.

Protein Kinase Assay

A radiometric protein kinase assay (33PANQINASE® Activity Assay, ProQinase) is used for measuring the kinase activity of the 320 protein kinases. All kinase assays are performed in 96-well FLASHPLATES' in a 50 µL reaction volume. The reaction cocktail is pipetted in 4 steps in the following order:
 1. 10 µL of non-radioactive ATP solution (in $H_2O$)
 2. 25 µL of assay buffer/[γ-33P]-ATP mixture
 3. 5 µL of test sample in 10% DMSO
 4. 10 µL of enzyme/substrate mixture The assay for all protein kinases contain 70 mM HEPES-NaOH pH 7.5, 3 mM $MgCl_2$, 3 mM $MnCl_2$, 3 µM Na-orthovanadate, 1.2 mM DTT, ATP (variable amounts, corresponding to the apparent ATP-Km of the respective kinase, see Table 1), [γ-33P]-ATP (approx. 8×1005 cpm per well), protein kinase (variable amounts; see Table 1), and substrate (variable amounts; see Table 1). All PKC assays (except the PKC-mu and the PKC-nu assay) additionally contain 1 mM $CaCl_2$, 4 mM EDTA, 5 µg/mL Phosphatidylserine and 1 µg/mL 1,2-Dioleyl-glycerol. The CAMK1D, CAMK2A, CAMK2B, CAMK2D, CAMK2G, CAMK4, CAMKK1, CAMKK2, DAPK2, EEF2K, MYLK, MYLK2 and MYLK3 assays additionally contain 1 µg/mL Calmodulin and 0.5 mM $CaCl_2$). The PRKG1 and PRKG2 assays additionally contain 1 µM cGMP. The DNA-PK assay additionally contained 2.5 µg/mL DNA.

The protein kinase reaction cocktails are incubated at 30° C. for 60 minutes. The reaction is stopped with 50 µL of 2% (v/v) $H_3PO_4$, plates are aspirated and washed two times with 200 µL 0.9% (w/v) NaCl. Incorporation of 33Pi (counting of "cpm") is determined with a microplate scintillation counter. All protein kinase assays are performed with a Beckman-Coulter BIOMEK® 2000/SL robotic system. All protein kinases provided by ProQinase are expressed in Sf9 insect cells or in *E. coli* as recombinant GST-fusion proteins or His-tagged proteins, either as full-length or enzymatically active fragments. All kinases are produced from human cDNAs and purified by either GSH-affinity chromatography or immobilized metal. Affinity tags are removed from a number of kinases during purification. The purity of the protein kinases is examined by SDS-PAGE/Coomassie staining, the identity is checked by mass spectroscopy. Kinases from external vendors (CAR=Carna Biosciences Inc.; INV=Life Technologies (Invitrogen Corporation™); MIL=Merck-Millipore (Millipore Corporation™), see Table 1) are expressed, purified and quality-controlled by virtue of the vendors readings. The concentrations of enzymes and substrates for the assays are shown in Table 1.

Evaluation of Raw Data

For each kinase, the median value of the cpm of three wells is defined as "low control" (n=3). This value reflects unspecific binding of radioactivity to the plate in the absence of a protein kinase but in the presence of the substrate. Additionally, for each kinase the median value of the cpm of three other wells is taken as the "high control", i.e. full activity in the absence of any inhibitor (n=3). The difference between high and low control of each enzyme is taken as 100% activity. As part of the data evaluation, the low control of each kinase is subtracted from the high control value as well as from their corresponding "compound values". The residual activity (in %) for each compound well is calculated by using the following formula: Res. Activity (%)=100× [(signal of compound−low control)/(high control−low control)]. Non Standard $IC_{50}$s are calculated using a customized excel spreadsheet in conjunction with XLFit Add-in. Due to the low number of data points, (4) XL-Fit calculates a non standard $IC_{50}$ using a four parametric equation where three parameters are locked to fixed values.
Equation is:

$$Y=B+((A-B))/[1+(x/C)]^{\wedge}D$$

A: Minimum value of activity, Also known as Bottom. Fixed to 0
B: Maximum value of activity, Also known as Top. Fixed to 100
C: Inflexion point of the curve
D: Hill Slope. Fixed to 1
Y: The dependent variable (i.e. what you measure as the signal)
X: The independent variable (i.e. what you control, such as, dose, concentration, etc.)

The way to calculate the Non Standard $IC_{50}$ is to assign random values to C parameter and repeat it iteratively. The algorithm then measures the differences in the sum of the residuals squared and will look for successive consecutive iterations where the change in the residuals is converging. Once the convergence limit has been met, the solution is regarded as the optimum and the fitting process ends.

CDK12 and CDK13 (ProQinase) are tested essentially as above but separately at 10 concentrations ($2\times10^5$ M to $6\times10^{10}$ M) using semi-logarithmic dilutions. For the 10 points, the analysis the residual activities for each concentration and the compound $IC_{50}$ values are calculated using QUATTRO® WORKFLOW™ V3.1.1. The fitting model for the $IC_{50}$ determinations was "Sigmoidal response (variable slope)" with parameters "top" fixed at 100% and "bottom" at 0%. The fitting method used was a least-squares fit. Data are shown in Table 1 below.

TABLE 1

| Kinase Name | Kinase Family | Kinase Conc. nM | ATP Conc. μM | Substrate Name | Substrate μg/50 μL | $IC_{50}$ μM |
|---|---|---|---|---|---|---|
| CDK7/CycH/MAT1 | CMGC | 3.3 | 3 | RBER-CHKtide | 2 | 0.0928 |
| CDK9/CycT1 | CMGC | 2.2 | 1 | RBER-CHKtide | 2 | 6.32 |
| CDK1/CycB1 | CMGC | 7 | 1 | RBER-CHKtide | 2 | 20.000 |
| CDK2/CycE1 | CMGC | 1.5 | 1 | RBER-CHKtide | 1 | 20.000 |
| CDK4/CycD1 | CMGC | 3.3 | 3 | RBER-CHKtide | 2 | 2.830 |
| CDK6/CycD1 | CMGC | 3.2 | 3 | RBER-CHKtide | 2 | 8.079 |
| CDK8/CycC | CMGC | 8.3 | 1 | RBER-IRStide | 1 | 10.922 |
| CDK16/CycY | CMGC | 3.2 | 0.3 | GSK3(14-27) | 2 | 9.073 |
| CDK19/CycC | CMGC | 30.9 | 3 | RBER-IRStide | 2 | 7.414 |
| CDK12/CycK | CMGC | 14.7 | 0.3 | RBER-IRStide | 2 | 14.780 |
| CDK13/CycK | CMGC | 29.2 | 0.3 | RBER-CDC25tide | 1 | 20.000 |

These data show that the compound of Example 1 is very selective for CDK7 from a representative panel of kinases.

Cell Proliferation Assay

The data in Table 2 shows that the compound of Example 1 inhibits proliferation and viability of the specified tumor cells lines. Cell lines are plated at the density 5000 cells per well in 100 μL per well growth medium into a white 96-well cell culture plate. See Table 2 for cell line and culture medium information. Plates are incubated at 37° C. and 5% $CO_2$. The following day, a serial dilution of the test compound is prepared by diluting the compound 1:3 in DMSO for 10 points. The DMSO plate is 1000× the final concentration. In addition to the CDK7 inhibitor, a DMSO alone column is included as a maximum growth control and 10 μM staurosporine final column is included as a maximum growth inhibition control. A 10× dilution plate is then prepared by adding 2 μL per well from the 1000×DMSO plate to 198 μL per well of OMEM (Life Technologies, Carlsbad, Calif., cat #31985-070). Cells are treated with indicated compound by adding 11 μL per well from the 10×OMEM plate to the cell plate containing 100 μL per well growth medium for a 1× final concentration. Plates are placed back into the incubator at 37° C. and 5% $CO_2$. Seven days after compound addition, plates are removed from the incubator and allowed to equilibrate to RT. CELL TITER GLO® reagent is thawed at room temperature and then prepare by mixing one vial of assay buffer with one vial of substrate and swirl gently to mix. CELL TITER GLO® reagent is then added to the cell plate, 100 μL per well, and place on a Titer Plate Shaker at speed setting 2 for 15 minutes at room temperature. After 15 minute incubation on shaker, luminescence is read, 1 second per well, using a Wallac VICTOR2™. Nonlinear regression and sigmoidal dose-response curves are used to calculate the half maximal inhibitory concentration ($IC_{50}$) with Graphpad Prism 6 software.

TABLE 2

| Cell Line | Histology | $IC_{50}$ (µM) | Catalog Number | Media Information |
|---|---|---|---|---|
| HCT116 | Colorectal Cancer | 0.04601 | ATCC# CCL-247 | McCoy's 5A (Gibco 16600) + 10% FBS (Hyclone SH30071.03) |
| MCF7 | Breast Cancer | 0.03201 | ATCC# HTB-22 | RPMI 1640 with L-Glutamine (Gibco 11875) + 10% FBS (Hyclone SH30071.03) |
| HCC1806 | Breast Cancer | 0.02553 | ATCC# CRL-2335 | RPMI 1640 with HEPES & L-Glutamine (Gibco 22400) + 10% FBS (Gibco cat#10082) |
| NCI-H460 | Lung Cancer | 0.0479 | ATCC# HTB-177 | RPMI 1640 with HEPES & L-Glutamine (Gibco 22400) + 10% FBS (Gibco cat#10082) |
| NCI-H446 | Lung Cancer | 0.01419 | ATCC# HTB-171 | RPMI 1640 with HEPES & L-Glutamine (Gibco 22400) + 1 mM Sodium Pyruvate (Gibco 11360) + 10% FBS (Hyclone SH30071.03) |
| A2780 | Ovarian Cancer | 0.02651 | ATCC# CRL-2772 | RPMI 1640 with L-Glutamine (Gibco 11875) + 10% FBS (Hyclone SH30071.03) |
| SNU-16 | Gastric Cancer | 0.02312 | ATCC# CRL-5974 | RPMI 1640 with HEPES & L-Glutamine (Gibco 22400) + 1 mM Sodium Pyruvate (Gibco 11360) + 10% FBS (Hyclone SH30071.03) |

These data show that the compound of Example I inhibits the in vitro growth of cancer cell lines from a variety of histologies including colon, breast, lung, ovary and stomach, in a dose dependent manner.

Xenograft Tumor Model

The purpose of this assay is to measure reduction in tumor volume in response to the compound of Example 1. To evaluate in vivo efficacy of a test compound, multiple xenograft tumor models are utilized. Briefly, 5-10×10⁶ tumor cells in a 1:1 MATRIGEL® mix (0.2 mL total volume) are injected subcutaneously into the female athymic nude mice (Envigo, Harlan laboratories) for a majority of xenograft tumor models. Alternate mice strains are utilized to establish MDAMB468 (NOD SCID Gamma, Jackson labs), CT26 and EMT6 (BALB/c, Envigo, Harlan Laboratories) xenografts. After allowing tumors to reach a desired size of ~300-500 mm³, animals are randomized into groups of 6-8 for efficacy studies. Test compound is administered via oral gavage (PO) at indicated doses and regimens. Tumor growth and body weight are monitored over time to evaluate efficacy and signs of toxicity.

Test compound is formulated in 5% N-methyl-2-pyrrolidone (NMP) in 1% hydroxyethylcellulose, 0.25% polysorbate 80, 0.05% antifoam in purified water (HEC) and administered by oral gavage (final volume 0.2 mL) at the doses indicated in Table 4. A test compound is formulated on a weekly basis and stored at 4° C. Vehicles are administered to the control groups according the schedules used above using a volume of 0.2 mL per dose. Mice are dosed via oral gavage and tumor samples are collected at termination and stored at −80° C.

Tumor size and body weight are recorded and analyzed bi-weekly. Blood is collected using DBS (dried blood spot) card 2 hours after dose and at termination. Tumors are collected at study termination, cut into 3 sections and either snap frozen for exposure and protein analysis, or placed in RNAlater® for RNA analysis. Tissue samples are frozen and stored at −80° C.

The compound of Example 1 demonstrates significant anti-tumor activity in human cancer xenograft models (Table 3).

TABLE 3

Summary of Example 1 in-vivo single-agent efficacy (ΔT/C) across variety of xenografts tumor models tested at different dose levels as indicated.

| Model | Histology | Mutations | Example 1 Dose (mg/kg) | Schedule | Avg. ΔT/C |
|---|---|---|---|---|---|
| A2780 | Ovary | ARID1A | 20 | QD × 35 | −41 |
| COLO205 | Ovary | | 20 | QD × 28 | −4 |
| CT26 | Colorectal | | 20 | QD × 24 | 52 |
| EMT6 | Breast | | 20 | QD × 28 | 17 |
| H441 | Lung | | 20 | QD × 35 | 0 |
| H460 | Lung | ARID1A | 20 | QD × 35 | 16 |
| HCC1806 | Breast | KMT2C | 20 | QD × 28 | −87 |
| HCT116 | Colorectal | KMT2C | 25 | QD × 21 | −17 |
| MDAMB468 | Breast | ARID1A, RB1 | 20 | QD × 28 | −91 |
| MIAPACA2 | Pancreatic | ARID1A | 20 | QD × 35 | 10 |
| MKN45 | Stomach | KMT2C | 20 | QD × 35 | 57 |
| MDAMB231 | Breast | | 20 | QD × 35 | −25 |

Delta T/C % is calculated when the endpoint tumor volume in a treated group is at or above baseline tumor volume. The formula is 100*(T−T0)/(C−C0). Here, T and C are mean endpoint tumor volumes in the treated or control group, respectively. T0 and C0 are mean baseline tumor volumes in those groups. *: Significant (p<0.05)

Biomarker Study

The purpose of this study is to evaluate potential predictive biomarkers for the compounds of the present invention.

Cancer cell lines are profiled to evaluate the anti-proliferative activity of a test compound in-vitro. Mutation, copy number and gene expression information of ARID1A, KMT2C, KMT2D and/or RB1 genes across cancer cell lines is obtained from COSMIC database (cancer.sanger.ac.uk) and cBioportal (http://www.cbioportal.org/). Cells are cultured in growth medium and plated into a 96-well plate in 100 μL/well growth medium at 5000 cells/well then incubated at 37° C., 5% $CO_2$ overnight. Cells are cultured using supplier recommended media and conditions well known in the art, for example with RPMI 1640 with or without HEPES & L-Glutamine (Thermo SH30255.01) and 1 mM Sodium Pyruvate, and 10% FBS (Gibco cat #10082). The 1000× intermediate dilution plate is prepared by making a 10 mM working solution of a test sample in DMSO and performing 1:3 dilutions in DMSO for 10 points. The 10× dosing plate is prepared by adding 2 μL from the 1000× intermediate dilution plate to 198 μL of OPTIMEM®+10% FBS and mixing well. The cell plate is then treated by adding 11 μL from the 10× dosing plate into the 100 μL/well cell plate for a 1× final concentration. Staurosporine is used as a maximum growth inhibition control at a final concentration of 5 μM. The cell plate is incubated for 7 days at 37° C., 5% $CO_2$. Seven days after treatment, Cell Titer-Glo® (Promega cat # G7571) assay buffer and substrate are removed from −20° C. and allowed to equilibrate to RT. Assay buffer is added to the substrate and swirled gently to mix. The CELL TITER-GLO® reagent (100 μL/well) is added to the cell plate and incubated at RT for 15 minutes. After 15 minutes, luminescence is read using a plate reader. Data is analyzed in Excel and graphed in GraphPad Prism. Statistical analysis and p value is calculated using Mann-Whitney nonparameteric t tests using GraphPad Prism.

A summary of proliferation data is shown in Table 4. Anti-proliferative effects of a test compound are categorized as insensitive ($IC_{50} \geq 1$ μM), cytostatic ($IC_{50} < 1$ μM and % inhibition<70%) or cytotoxic ($IC_{50} < 1$ μM and % inhibition≥70%). Cell lines carrying inactivating or loss of function (LOF) mutations in either ARID1A, KMT2C, KMT2D or RB1 gene demonstrated significantly greater cytotoxic response to Example 1 compared to the rest of the cell lines in the panel (Table 5). In contrast, non-LOF cell lines demonstrated a higher (%) of cytostatic response in response to Example 1.

Furthermore, a number of xenograft tumor models carrying these mutations were utilized to evaluate the efficacy of Example 1 as a monotherapy (Table 3).

A summary of efficacy studies and anti-tumor activity (ΔT/C) is shown in Table 3. Example 1 demonstrated robust efficacy in a variety of tumor models, with significant regressions noted in the tumor models harboring mutations in ARID1A, KMT2C or RB1 genes. Taken together, these findings show that inactivating mutations in the ARID1A, KMT2C, KMT2D or RB1 gene presents a potential patient selection strategy for treatment with Example 1 across multiple cancer types.

TABLE 4

Summary of Example 1 anti-proliferative log-$GI_{50}$ (nM) and Growth-Inhibition (%) across variety of cancer cell lines as indicated. Cell lines treated for 7 days and analyzed using CellTiter-Glo ® assay.

| | | | Anti-proliferation effect | | | | | | |
| | | | $IC_{50}$ | % | | LOF Mutations in Gene(s) | | | |
| Cell Line | Media Information | Histology | (μM) | Inh. | Outcome | ARID1A | KMT2C | KMT2D | RB1 |
|---|---|---|---|---|---|---|---|---|---|
| 22RV1 | A | PROSTATE | 0.028 | 77 | Cytotoxic | Yes | | | |
| A2058 | B | SKIN | 0.030 | 97 | Cytotoxic | | | | Yes |
| A2780 | C | OVARY | 0.052 | 74 | Cytotoxic | Yes | | | |
| A375 | B | SKIN | 0.055 | 86 | Cytotoxic | | | | |
| A549 | D | LUNG | 0.139 | 64 | Cytostatic | | | | |
| A673 | B | BONE | 0.014 | 96 | Cytotoxic | | | | |
| AN3CA | E | ENDOMETRIUM | 0.050 | 67 | Cytostatic | Yes | | | |
| AZ521 | F | STOMACH | 0.036 | 76 | Cytotoxic | | | | |
| BT20 | B | BREAST | 0.373 | 45 | Cytostatic | | | | |
| C33A | F | ENDOMETRIUM | 0.014 | 79 | Cytotoxic | Yes | | Yes | |
| CACO2 | B | INTESTINE | 0.189 | 60 | Cytostatic | | | | |
| CAOV3 | B | OVARY | 0.019 | 96 | Cytotoxic | | Yes | | Yes |
| CCRFCEM | C | BLOOD | 0.040 | 96 | Cytotoxic | | | | |
| COLO201 | C | INTESTINE | 0.123 | 61 | Cytostatic | | | | |
| COLO320 | C + 0.8 ug/mL Puromycin | INTESTINE | 0.189 | 73 | Cytotoxic | | | | |
| CORL311 | C | LUNG | 0.095 | 75 | Cytotoxic | | | | |
| CORL88 | C | LUNG | 4.200 | 34 | Insensitive | | | | Yes |
| COV318 | C | OVARY | >10 | 40 | Insensitive | | | | |
| CT26 | C + 0.8 ug/mL Puromycin | INTESTINE | >10 | −47 | Insensitive | | | | |
| DMS114 | C | LUNG | 0.014 | 65 | Cytostatic | | | | |
| DMS273 | G | LUNG | 0.019 | 80 | Cytotoxic | | | | Yes |
| DMS53 | C | LUNG | 0.118 | 66 | Cytostatic | | | | |
| DMS79 | C + 0.8 ug/mL Puromycin | LUNG | 0.354 | 50 | Cytostatic | | | | Yes |
| DU145 | F | PROSTATE | 0.036 | 74 | Cytotoxic | | Yes | | Yes |
| EBC1 | C + 1 ug/mL Puromycin | LUNG | 0.047 | 83 | Cytotoxic | | | | |
| EGL1 | H | | 0.041 | 95 | Cytotoxic | | | | |
| EVSAT | G + 2 ug/mL Puromycin | BREAST | 0.040 | 79 | Cytotoxic | | | | Yes |
| GL261 | C | BRAIN | 0.038 | 85 | Cytotoxic | | | | |
| HCC1143 | C | BREAST | >10 | 37 | Insensitive | Yes | | | |
| HCC1187 | I | BREAST | 0.027 | 73 | Cytotoxic | | | | Yes |
| HCC1569 | C | BREAST | 0.067 | 45 | Cytostatic | | | | Yes |
| HCC1806 | C | BREAST | 0.014 | 99 | Cytotoxic | | Yes | | |

TABLE 4-continued

Summary of Example 1 anti-proliferative log-GI$_{50}$ (nM) and Growth-Inhibition (%) across variety of cancer cell lines as indicated. Cell lines treated for 7 days and analyzed using CellTiter-Glo ® assay.

| Cell Line | Media Information | Histology | IC$_{50}$ (μM) | % Inh. | Outcome | ARID1A | KMT2C | KMT2D | RB1 |
|---|---|---|---|---|---|---|---|---|---|
| HCC2218 | C | BREAST | 0.560 | 41 | Cytostatic | | | | Yes |
| HCC4006 | C | LUNG | 0.028 | 57 | Cytostatic | | | | |
| HCC44 | C | LUNG | 0.131 | 48 | Cytostatic | | | | |
| HCC70 | I | BREAST | 0.038 | 89 | Cytotoxic | | | | Yes |
| HCC827 | C | LUNG | 0.055 | 69 | Cytotoxic | | | | |
| HCT116 | J | INTESTINE | 0.041 | 88 | Cytotoxic | | Yes | | |
| HCT8 | C | INTESTINE | 0.981 | 3 | Cytostatic | | | | |
| HEC108 | F | ENDOMETRIUM | 0.031 | 90 | Cytotoxic | Yes | Yes | | |
| HEC1A | J | ENDOMETRIUM | 0.162 | 56 | Cytostatic | Yes | Yes | | |
| HEP3B217 | F | LIVER | 0.033 | 66 | Cytostatic | | | | Yes |
| HEPG2 | F | LIVER | 0.028 | 78 | Cytotoxic | | | | |
| HEYA8 | C | OVARY | 0.112 | 89 | Cytotoxic | Yes | Yes | Yes | |
| HGC27 | F | STOMACH | 0.068 | 78 | Cytotoxic | | | | |
| HL60 | C | BLOOD | 0.045 | 87 | Cytotoxic | | | | |
| HLE | B | LIVER | 0.030 | 77 | Cytotoxic | | Yes | | Yes |
| HLF | B | LIVER | 0.017 | 100 | Cytotoxic | | Yes | | Yes |
| HOS | C | BONE | 0.090 | 72 | Cytotoxic | | Yes | | |
| HS294T | K | SKIN | 0.020 | 84 | Cytotoxic | | | | |
| HS766T | L | PANCREAS | 0.062 | 72 | Cytotoxic | Yes | | | |
| HT | C | BLOOD | 0.131 | 64 | Cytostatic | | | | |
| HT1197 | E | URINARY | 0.281 | 55 | Cytostatic | Yes | | Yes | |
| HUH1 | M | LIVER | 0.128 | 72 | Cytotoxic | Yes | | | |
| HUH28 | A | BILIARY | 2.896 | 32 | Insensitive | Yes | | | Yes |
| HUH7 | N | LIVER | 0.175 | 64 | Cytotoxic | | | | |
| IGROV1 | C | OVARY | 0.072 | 70 | Cytotoxic | Yes | Yes | | |
| IMR32 | O | CNS | 0.002 | 100 | Cytotoxic | Yes | | | |
| JHH4 | B | LIVER | 0.166 | 65 | Cytostatic | | | | |
| JHH7 | C | LIVER | 0.027 | 88 | Cytotoxic | | | | |
| JURKAT | P | BLOOD | 0.061 | 98 | Cytotoxic | Yes | Yes | | |
| K562 | C | BLOOD | >10 | −191 | Insensitive | | | | |
| Karpas1106 | C | BLOOD | 0.026 | 98 | Cytotoxic | | | | |
| KARPAS299 | C | BLOOD | 0.069 | 78 | Cytotoxic | | | | |
| KE97 | C | BLOOD | 0.158 | 58 | Cytostatic | | | | |
| KELLY | C | CNS | 0.058 | 80 | Cytotoxic | | | | |
| KLE | Q | ENDOMETRIUM | 0.028 | 65 | Cytostatic | | Yes | | Yes |
| KP4 | L | PANCREAS | 0.036 | 65 | Cytostatic | | | | |
| KPL1 | G + 2 ug/mL Puromycin | BREAST | 0.668 | 43 | Cytostatic | | | | |
| KURAMOCHI | C | OVARY | 0.052 | 88 | Cytotoxic | | | | |
| KYSE150 | R | OESOPHAGUS | 0.042 | 64 | Cytostatic | | | | |
| KYSE180 | C | OESOPHAGUS | 0.103 | 68 | Cytostatic | | | | |
| KYSE270 | R | OESOPHAGUS | >10 | −180 | Insensitive | | | | Yes |
| KYSE30 | S | OESOPHAGUS | 0.076 | 76 | Cytotoxic | | | | |
| KYSE520 | C | OESOPHAGUS | >10 | 50 | Insensitive | | | | |
| KYSE70 | C | OESOPHAGUS | 0.126 | 70 | Cytotoxic | Yes | | | |
| LI7 | M | LIVER | 0.132 | 76 | Cytotoxic | | | | |
| LN18 | T | CNS | 0.015 | 91 | Cytotoxic | | Yes | | |
| LN229 | T | CNS | 0.036 | 63 | Cytostatic | | | | |
| LNCAP | P | PROSTATE | 0.059 | 74 | Cytotoxic | Yes | Yes | | |
| LS411N | C | INTESTINE | 1.000 | 45 | Insensitive | Yes | Yes | | |
| M14 | L | SKIN | 0.032 | 85 | Cytotoxic | Yes | | | |
| MCF7 | F | BREAST | 0.155 | 58 | Cytostatic | | | | |
| MDAMB157 | P | BREAST | 0.866 | 39 | Cytostatic | | | | |
| MDAMB231 | U | BREAST | 2.816 | 23 | Insensitive | | | | |
| MDAMB453 | U | BREAST | 0.039 | 56 | Cytostatic | | | | |
| MDAMB468 | B | BREAST | 0.008 | 100 | Cytotoxic | Yes | | | Yes |
| MDAPCA2B | U | PROSTATE | 6.273 | 17 | Insensitive | | Yes | | |
| MDST8 | B | INTESTINE | 0.049 | 88 | Cytotoxic | | | | |
| MHCC97H | V | LIVER | 0.243 | 59 | Cytostatic | | | | |
| MHCC97L | V | LIVER | 0.526 | 45 | Cytostatic | | | | |
| MKN1 | C | STOMACH | 0.023 | 80 | Cytotoxic | | | | |
| MKN45 | C | STOMACH | 0.056 | 79 | Cytotoxic | Yes | | | |
| MKN7 | C | STOMACH | >10 | 39 | Insensitive | | | Yes | |
| MKN74 | C | STOMACH | 0.073 | 71 | Cytotoxic | | | | Yes |
| MOLT4 | C | BLOOD | 0.040 | 99 | Cytotoxic | | Yes | Yes | |
| MX1 | C | BREAST | 0.045 | 72 | Cytotoxic | | | | Yes |
| NCIH1048 | W | LUNG | 0.004 | 95 | Cytotoxic | | Yes | | Yes |
| NCIH1092 | C | LUNG | 0.683 | 42 | Cytostatic | | | | |
| NCIH1155 | B | LUNG | 0.043 | 51 | Cytostatic | | | | Yes |
| NCIH1299 | A | LUNG | 0.195 | 44 | Cytostatic | | | | |
| NCIH1436 | C | LUNG | 0.195 | 56 | Cytostatic | Yes | | | |

TABLE 4-continued

Summary of Example 1 anti-proliferative log-GI$_{50}$ (nM) and Growth-Inhibition (%) across variety of cancer cell lines as indicated. Cell lines treated for 7 days and analyzed using CellTiter-Glo ® assay.

| | | | Anti-proliferation effect | | | LOF Mutations in Gene(s) | | | |
|---|---|---|---|---|---|---|---|---|---|
| Cell Line | Media Information | Histology | IC$_{50}$ (μM) | % Inh. | Outcome | ARID1A | KMT2C | KMT2D | RB1 |
| NCIH146 | C + 0.8 ug/mL Puromycin | LUNG | 0.030 | 77 | Cytotoxic | | | | Yes |
| NCIH1666 | C | LUNG | 0.161 | 59 | Cytostatic | | | | |
| NCIH1703 | C | LUNG | 0.040 | 92 | Cytotoxic | | | | |
| NCIH1734 | C | LUNG | 0.024 | 76 | Cytotoxic | | | | Yes |
| NCIH1975 | C | LUNG | 0.021 | 90 | Cytotoxic | | | | Yes |
| NCIH2030 | X | LUNG | 5.374 | 9 | Insensitive | | | | |
| NCIH2081 | W | LUNG | 0.442 | 44 | Cytostatic | | | Yes | Yes |
| NCIH209 | C + 0.8 ug/mL Puromycin | LUNG | 0.040 | 83 | Cytotoxic | | | | |
| NCIH2122 | C | LUNG | 0.078 | 85 | Cytotoxic | | | | |
| NCIH2196 | C | LUNG | 0.123 | 63 | Cytostatic | | | | Yes |
| NCIH2228 | C | LUNG | 0.276 | 57 | Cytostatic | | | | Yes |
| NCIH226 | C | LUNG | 1.197 | 43 | Insensitive | | | | |
| NCIH2347 | C + 0.8 ug/mL Puromycin | LUNG | 0.661 | 45 | Cytostatic | | | | |
| NCIH358 | C | LUNG | 0.042 | 93 | Cytotoxic | | | | |
| NCIH441 | C | LUNG | 0.014 | 84 | Cytotoxic | | | | |
| NCIH446 | C | LUNG | 0.013 | 95 | Cytotoxic | | | Yes | Yes |
| NCIH460 | C | LUNG | 0.047 | 97 | Cytotoxic | Yes | | | |
| NCIH520 | C | LUNG | 0.082 | 77 | Cytotoxic | | | | |
| NCIH522 | C | LUNG | 0.107 | 50 | Cytostatic | | | | |
| NCIH524 | C | LUNG | 0.037 | 92 | Cytotoxic | | | | Yes |
| NCIH526 | C | LUNG | 0.018 | 94 | Cytotoxic | | | | |
| NCIH596 | C | LUNG | 0.922 | 46 | Cytostatic | | | | Yes |
| NCIH69 | C | LUNG | 0.173 | 68 | Cytostatic | | | | Yes |
| NCIH727 | C | LUNG | 0.117 | 56 | Cytostatic | | | | |
| NCIH82 | C | LUNG | 0.699 | 22 | Cytostatic | | | | Yes |
| NIHOVCAR3 | Y | OVARY | 0.040 | 96 | Cytotoxic | | | | |
| NUGC3 | C | STOMACH | 0.030 | 81 | Cytotoxic | Yes | Yes | Yes | |
| NUGC4 | C | STOMACH | 0.019 | 83 | Cytotoxic | | | | |
| OAW42 | Z | OVARY | 0.136 | 88 | Cytotoxic | Yes | | | |
| OCUM1 | N | STOMACH | 0.027 | 82 | Cytotoxic | Yes | | | |
| OV90 | C | OVARY | 0.034 | 61 | Cytostatic | | | | |
| OVCAR5 | Y | OVARY | 0.086 | 74 | Cytotoxic | | | | |
| OVCAR8 | C | OVARY | 0.065 | 90 | Cytotoxic | | | | Yes |
| OZ | AA | LIVER | 0.050 | 77 | Cytotoxic | | | | |
| PANC1 | L | PANCREAS | 0.071 | 47 | Cytostatic | | | | |
| PATU8988T | C | PANCREAS | 0.201 | 55 | Cytostatic | | | | |
| PLCPRF5 | BB | LIVER | >10 | 41 | Insensitive | | | | |
| Raw264.7 | C | | 0.355 | 62 | Cytostatic | | | | |
| RKO | B | INTESTINE | 0.118 | 61 | Cytostatic | Yes | | | |
| RT112 | P | URINARY | 0.032 | 87 | Cytotoxic | | | | |
| SAOS2 | CC | BONE | 0.028 | 66 | Cytostatic | | | | Yes |
| SH10TC | C | STOMACH | 0.147 | 58 | Cytostatic | | | | Yes |
| SHSY5Y | DD | CNS | 0.059 | 95 | Cytotoxic | | | | |
| SiHa | F | ENDOMETRIUM | 0.105 | 58 | Cytostatic | | | | |
| SJRH30 | C | SOFT TISSUE | 0.039 | 62 | Cytostatic | | | | |
| SKHEP1 | BB | LIVER | 0.118 | 71 | Cytotoxic | | | | |
| SKMEL28 | B | SKIN | 0.098 | 61 | Cytostatic | | | | |
| SKMES1 | F | LUNG | 0.028 | 80 | Cytotoxic | | | Yes | |
| SKOV3 | J | OVARY | >10 | 27 | Insensitive | Yes | | | |
| SKUT1 | E | SOFT TISSUE | 0.041 | 89 | Cytotoxic | Yes | | | Yes |
| SNU1 | C | STOMACH | 0.105 | 68 | Cytotoxic | Yes | Yes | | |
| SNU1079 | EE | BILIARY | 0.038 | 89 | Cytotoxic | Yes | | | |
| SNU1196 | EE | BILIARY | 0.043 | 68 | Cytostatic | | | | |
| SNU16 | C | STOMACH | 0.017 | 84 | Cytotoxic | | | | Yes |
| SNU245 | EE | BILIARY | 1.089 | −5 | Insensitive | | | | |
| SNU308 | EE | BILIARY | 0.184 | 61 | Cytostatic | | | | |
| SNU387 | X | LIVER | >10 | 12 | Insensitive | | | | |
| SNU398 | M | LIVER | 0.021 | 85 | Cytotoxic | | | | |
| SNU423 | M | LIVER | >10 | 40 | Insensitive | Yes | | | |
| SNU449 | C | LIVER | 1.521 | 8 | Insensitive | Yes | | | |
| SNU475 | M | LIVER | 3.917 | 28 | Insensitive | | | | |
| SNU478 | EE | BILIARY | 0.032 | 92 | Cytotoxic | | | | Yes |
| SNU5 | FF | STOMACH | 0.039 | 79 | Cytotoxic | Yes | | | |
| SNU739 | C | LIVER | >10 | 47 | Insensitive | | | | |
| SNU869 | EE | BILIARY | 0.052 | 60 | Cytostatic | | | | |
| SW1271 | U | LUNG | 0.024 | 67 | Cytostatic | | | | |
| SW48 | U | INTESTINE | 0.005 | 89 | Cytotoxic | Yes | Yes | | |
| SW480 | U | INTESTINE | 0.036 | 90 | Cytotoxic | Yes | | Yes | |

TABLE 4-continued

Summary of Example 1 anti-proliferative log-GI$_{50}$ (nM) and Growth-Inhibition (%) across variety of cancer cell lines as indicated. Cell lines treated for 7 days and analyzed using CellTiter-Glo ® assay.

| | | | Anti-proliferation effect | | | LOF Mutations in Gene(s) | | | |
|---|---|---|---|---|---|---|---|---|---|
| Cell Line | Media Information | Histology | IC$_{50}$ (μM) | % Inh. | Outcome | ARID1A | KMT2C | KMT2D | RB1 |
| SW626 | U | | 1.105 | 39 | Insensitive | | | | |
| SW780 | U | URINARY | 0.074 | 68 | Cytostatic | | | | |
| SW837 | U | INTESTINE | 0.068 | 55 | Cytostatic | | | | |
| SW900 | U | LUNG | 3.806 | 13 | Insensitive | | | | |
| T47D | GG | BREAST | 0.045 | 68 | Cytostatic | Yes | | | |
| T84 | HH | INTESTINE | 0.308 | 61 | Cytostatic | | | | Yes |
| T98G | O | CNS | 1.371 | 44 | Insensitive | | | | |
| TCCSUP | E | URINARY | 0.040 | 61 | Cytostatic | Yes | | | |
| TFK1 | II | BILIARY | 0.040 | 87 | Cytotoxic | | | | |
| TGW | O | BRAIN | 0.070 | 63 | Cytostatic | | | | |
| THP1 | C | BLOOD | 0.042 | 81 | Cytotoxic | | | | |
| TOV112D | JJ | OVARY | 0.025 | 81 | Cytotoxic | | | | |
| TOV21G | C | OVARY | 0.061 | 73 | Cytotoxic | Yes | Yes | | |
| TYKNU | O | OVARY | 0.072 | 83 | Cytotoxic | | Yes | | |
| U118MG | B | CNS | 1.170 | 42 | Insensitive | | | | |
| U87MG | O | CNS | 7.356 | −5 | Insensitive | | | | |
| UACC812 | U | BREAST | 0.076 | 58 | Cytostatic | Yes | | | |
| UACC893 | U | BREAST | 4.150 | −51 | Insensitive | | | | Yes |
| UMUC3 | E | URINARY | 0.161 | 70 | Cytotoxic | | | | |
| ZR751 | C | BREAST | 0.043 | 69 | Cytostatic | | | | |

Media Information:
A. RPMI 1640 (Gibco 11835, Gibco 22400-089, or Hyclone Cat # SH30027) + 10% FBS (Gibco cat#10082)
B. DMEM with L-Glutamine (Thermo cat#SH30022) + NaPyr + NEAA + HEPES + 10% FBS (Gibco cat#10082)
C. RPMI 1640 with HEPES & L-Glutamine (Gibco 22400) + 1 mM Na Pyruvate + 10% FBS(Gibco cat#10082)
D. F-12K Medium (Cat#30-2004) + 10% FBS (Gibco cat#10082)
E. EMEM (CellGro cat#17-305-CV) + L-Glutamine + Na Pyruvate + Na Bicarbonate + 10% FBS (Gibco cat#10082)
F. EMEM (CellGro cat#17-305-CV) + L-Glutamine + Na Pyruvate + Na Bicarbonate + NEAA+ 10% FBS (Gibco cat#10082)
G. DMEM (Gibco 11995) + 1 mM Na Pyruvate + 10% FBS(Gibco cat#10082)
H. DMEM High Glucose (Hyclone Cat # SH30022) + 10% HI FBS (Gibco Cat # 10082) + 1X NEAA (Hyclone SH30328)
I. ATCC modified RPMI 1640 (Gibco A1049101) + 1 mM Na Pyruvate + 10% FBS(Gibco cat#10082)
J. McCoy's 5A + 10% FBS (Gibco cat#10082)
K. DMEM (Gibco 11965) + 10% FBS
L. MEM Eagle with Earle's Salts (Gibco 11095-080) + 1% NEAA + 1% NaPyr + 10% FBS (Gibco cat#10082)
M. RPMI-1640 with L-glutamine and HEPES + 10% heat inactivated FBS
N. DMEM with L-Glutamine (Thermo cat#SH30022) + Na Pyruvate + 10% FBS (Gibco cat#10082)
O. MEM (Gibco 11095) + Na Pyruvate + NEAA + 10% FBS (Gibco cat#10082)
P. RPMI 1640 with HEPES & L-Glutamine (Thermo SH30255.01 or Gibco 11835) + 1 mM Sodium Pyruvate + 10% FBS(Gibco cat#10082)
Q. DMEM:F12 w/2.5 mM L-glutamine, 15 mM HEPES + 0.5 mM NaPyruv + 10% FBS
R. 49% RPMI 1640 + 49% Ham's F12 + 2% h.i. FBS
S. 45% RPMI 1640 + 45% Ham's F12 + 10% h.i. FBS
T. DMEM (Gibco 11965) + 1 mM Na Pyruvate + 5% FBS (Gibco cat#10082)
U. Leibovitz's L15 (Gibco cat#11415-064) + 10% FBS (Gibco cat#10082), No CO$_2$
V. DMEM with high Glu & L-gln + 10% heat inactivated FBS + NaPyr + NEAA + HEPES
W. DMEM:F12 (1:1) + ITS + 10 nM Hydrocortisone + 10 nM beta-Estradiol + 4.5 mM L-glut + 5% FBS (Gibco cat#10082)
X. RPMI-1640 with L-glutamine and HEPES + 10% FBS
Y. RPMI 1640 with HEPES & L-Glutamine (Gibco 22400) + 1 mM Na Pyruvate + NEAA + 20% FBS(Gibco cat#10082)
Z. DMEM + 2 mM Glutamine + 1 mM Sodium Pyruvate (NaP) + 20 IU/l Bovine Insulin + 10% FBS(Gibco cat#10082)
AA. Williams' E media (Gibco Cat # 12551) + 10% FBS
BB. MEM + 10% FBS + NaPyr + NEAA + HEPES + 1.5 g/L NaHCO$_3$
CC. McCoy's 5A (Gibco 16600) + 15% FBS (Gibco cat#10082)
DD. 1:1 MEM (11095):F12 (CellGro 10-080-CV) + 10% FBS (Gibco cat#10082)
EE. RPMI-1640 with glutamine and HEPES (Hyclone Cat # SH30255) + 10% FBS (Gibco Cat # 16000) + 1X NaPyr
FF. Iscove's modified Dulbecco's medium w/L-glutamine, 25 mM HEPES [GIBCO 12440-053] + 20% FBS
GG. RPMI 1640 with HEPES & L-Glutamine (phenol-red-free) + 1 mM Na Pyruvate + 10% FBS(Gibco cat#10082)
HH. 1:1 Hams F12:DMEM + L-Glutamine + 5% FBS (Gibco cat#10082)
II. RPMI-1640 (Hyclone Cat # SH30027) + 10% Heat inactivted FBS (Gibco Cat # 10082)
JJ. 1:1 mixture of MCDB 105 medium containing a final concentration of 1.5 g/L sodium bicarbonate and Medium 199 containing a final concentration of 2.2 g/L sodium bicarbonate + 15% FBS

TABLE 5

Distribution (%) of anti-proliferation effects of Example 1 across cancer cell lines carrying LOF mutations.

| | Cytotoxic (IC$_{50}$ < 1 μM, % Inh. ≥70) | Cytostatic (IC$_{50}$ < 1 μM, % Inh. <70) | Insensitive (IC$_{50}$ ≥ 1 μM, % Inh. <70) |
|---|---|---|---|
| ARID1A mutants | 64%, n = 25 | 23%, n = 9 | 13%, n = 5 |
| KMT2D mutants | 76%, n = 19 | 12%, n = 3 | 12%, n = 3 |
| KMT2C mutants | 70%, n = 7 | 20%, n = 2 | 10%, n = 1 |
| RB1 mutants | 54%, n = 22 | 37%, n = 15 | 10%, n = 4 |
| Others | 40%, n = 41 | 44%, n = 45 | 17%, n = 17 |

We claim:

1. A method for inhibiting cyclin-dependent kinase 7 activity in a patient, comprising administering to the patient in need thereof a therapeutically effective amount of a compound of formula (I):

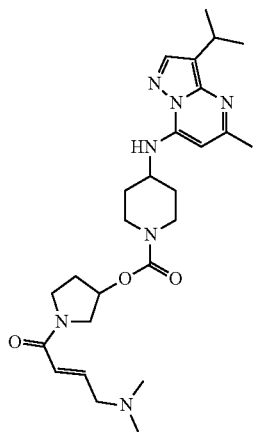

or a pharmaceutically acceptable salt or enantiomer thereof.

2. The method according to claim 1, wherein the patient has a cancer selected from the group consisting of a glioma, a sarcoma, breast cancer, cervical cancer, colorectal cancer, gastric cancer, hematological cancer, hepatobiliary cancer, lung cancer, ovarian cancer, pancreatic cancer, prostate cancer, skin cancer, urothelial cancer, and uterine cancer.

3. The method according to claim 2, wherein the patient has a cancer selected from the group consisting of breast cancer, colorectal cancer, gastric cancer, lung cancer, and ovarian cancer.

4. The method according to claim 1, wherein the compound is the (S)-enantiomer of formula (II):

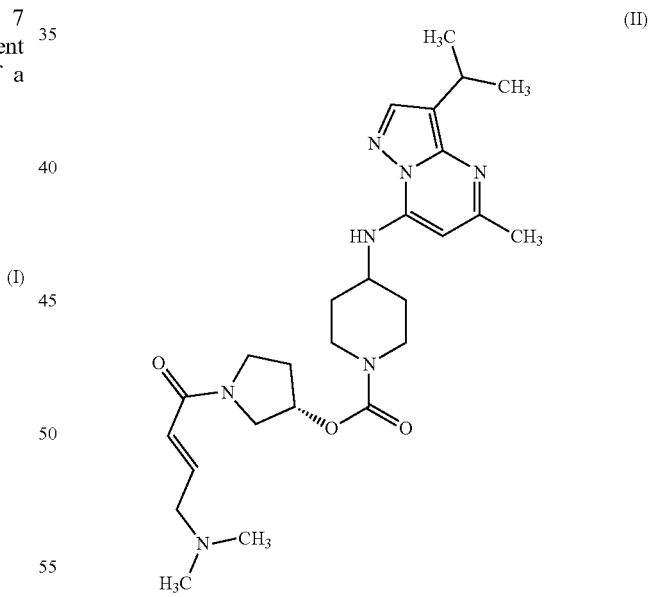

or a pharmaceutically acceptable salt thereof.

5. The method according to claim 4, wherein:
   (a) the pharmaceutically acceptable salt is the besylate salt; or
   (b) the pharmaceutically acceptable salt is the hemi-edisylate monohydrate salt.

6. The method according to claim 5, wherein the besylate salt is characterized by a powder X-ray diffraction pattern (using Cu-Kα radiation) having a powder X-ray diffraction peak at an angle (2θ) of 21.5°±0.2°, in combination with one or more additional powder X-ray diffraction peaks at angles (2θ) selected from the group consisting of 12.4°±0.2°, 15.8°±0.2°, and 17.3°±0.2°.

7. The method according to claim 5, wherein the hemi-edisylate monohydrate salt is characterized by a powder X-ray diffraction pattern (using Cu-Kα radiation) having powder X-ray diffraction peak at an angle (2θ) of 18.5°±0.2°, in combination with one or more additional powder X-ray diffraction peaks at angles (2θ) selected from the group consisting of 15.2°±0.2°, 16.7°±0.2°, and 21.5°±0.2°.

8. The method according to claim 1, wherein the compound is the (S)-enantiomer of formula (II):

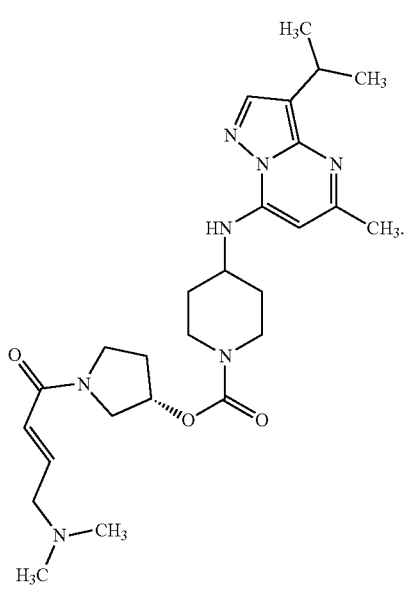

9. A method for inhibiting cyclin-dependent kinase 7 activity in a patient, comprising:
   (a) testing for the presence of at least one loss of function mutation in the ARID1A, KMT2C, KMT2D, or RB1 gene in a biological sample from the patient; and
   (b) administering to the patient in need thereof who tests positive for the loss of function mutation a therapeutically effective amount of a compound of formula (I):

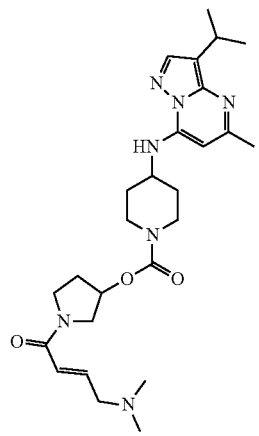

or a pharmaceutically acceptable salt or enantiomer thereof.

10. The method according to claim 9, wherein:
   (a) the biological sample is a tumor sample; and
   (b) the tumor sample is assayed by genomic sequencing or DNA sequencing.

11. The method according to claim 9, wherein the patient has a cancer selected from the group consisting of a glioma, a sarcoma, breast cancer, cervical cancer, colorectal cancer, gastric cancer, hematological cancer, hepatobiliary cancer, lung cancer, ovarian cancer, pancreatic cancer, prostate cancer, skin cancer, urothelial cancer, and uterine cancer.

12. The method according to claim 11, wherein the patient has a cancer selected from the group consisting of breast cancer, colorectal cancer gastric cancer lung cancer, and ovarian cancer.

13. The method according to claim 9, wherein the compound is the (S)-enantiomer of formula (II):

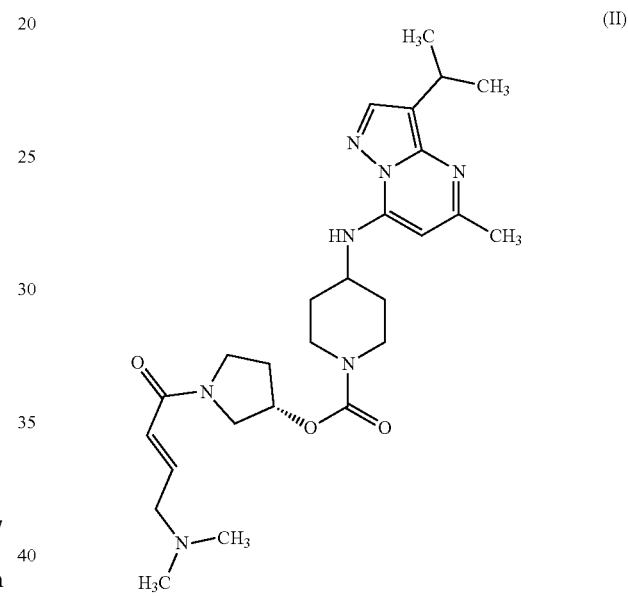

or a pharmaceutically acceptable salt thereof.

14. The method according to claim 13, wherein:
   (a) the pharmaceutically acceptable salt is the besylate salt; or
   (b) the pharmaceutically acceptable salt is the hemi-edisylate monohydrate salt.

15. The method according to claim 14, wherein the besylate salt is characterized by a powder X-ray diffraction pattern (using Cu-Kα radiation) having a powder X-ray diffraction peak at an angle (2θ) of 21.5°±0.2°, in combination with one or more additional powder X-ray diffraction peaks at angles (2θ) selected from the group consisting of 12.4°±0.2°, 15.8°±0.2°, and 17.3°±0.2°.

16. The method according to claim 14, wherein the hemi-edisylate monohydrate salt is characterized by a powder X-ray diffraction pattern (using Cu-Kα radiation) having powder X-ray diffraction peak at an angle (2θ) of 18.5°±0.2°, in combination with one or more additional powder X-ray diffraction peaks at angles (2θ) selected from the group consisting of 15.2°±0.2°, 16.7°±0.2°, and 21.50±0.2°.

17. The method according to claim 9, wherein the compound is the (S)-enantiomer of formula (II):

(II)
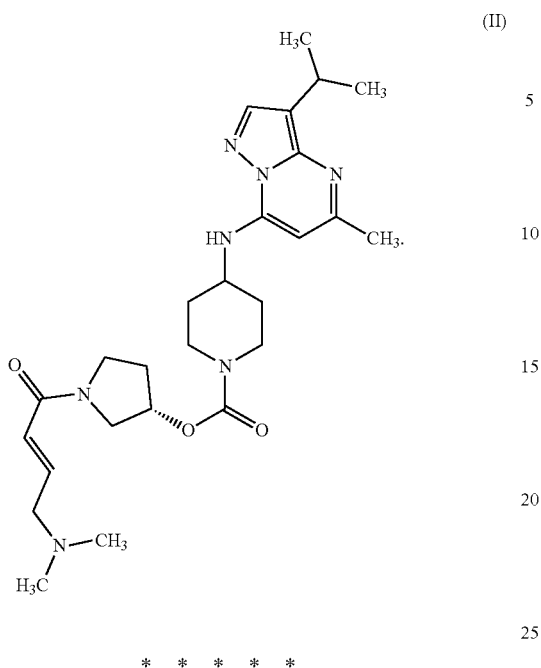

UNITED STATES PATENT AND TRADEMARK OFFICE
CERTIFICATE OF CORRECTION

PATENT NO. : 10,787,460 B2  
APPLICATION NO. : 16/583661  
DATED : September 29, 2020  
INVENTOR(S) : David Andrew Coates et al.

Page 1 of 3

It is certified that error appears in the above-identified patent and that said Letters Patent is hereby corrected as shown below:

On the Title Page

Item (72), In Column 1, Line 5-6: Delete "Yipin Yadav" and insert -- Vipin Yadav --, therefor.

Item (56), In Column 2, Line 2: Delete "Hackann," and insert -- Hackam, --, therefor.

In the Claims

In Claim 1, Column 47, Lines 44-62: Delete " 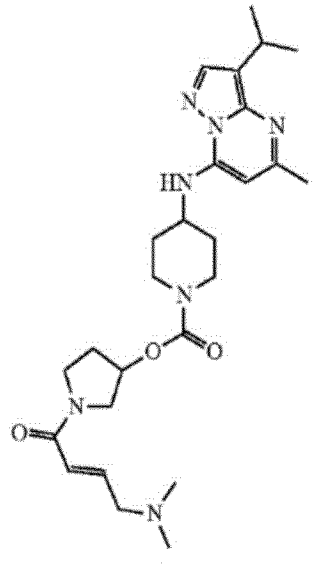 " and insert

Signed and Sealed this  
Fifth Day of January, 2021

Andrei Iancu  
*Director of the United States Patent and Trademark Office*

CERTIFICATE OF CORRECTION (continued)
U.S. Pat. No. 10,787,460 B2

Page 2 of 3

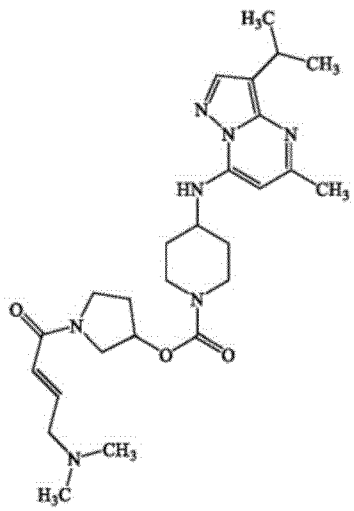

-- --, therefor.

In Claim 7, Column 49, Line 10: Delete "21.5" and insert -- 21.5° --, therefor.

In Claim 9, Column 49, Lines 47-65: Delete " 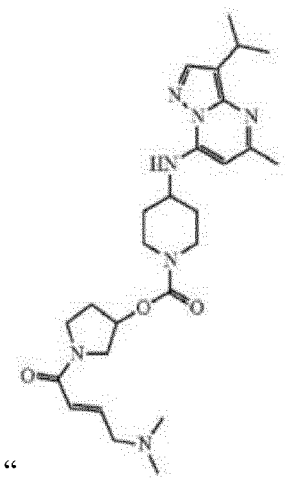 "

and insert -- 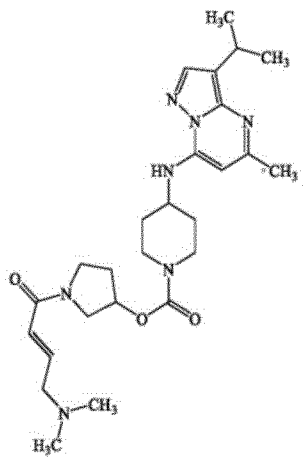 --, therefor.
In Claim 12, Column 50, Line 14: Delete "colorectal cancer gastric cancer" and insert -- colorectal cancer, gastric cancer, --, therefor.
In Claim 16, Column 50, Line 65: Delete "21.50" and insert -- 21.5° --, therefor.

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25
```